(12) United States Patent
Isaji

(10) Patent No.: US 6,933,883 B2
(45) Date of Patent: Aug. 23, 2005

(54) METHOD AND DEVICE FOR ALIGNING RADAR MOUNT DIRECTION, AND RADAR ALIGNED BY THE METHOD OR DEVICE

(75) Inventor: Osamu Isaji, Kobe (JP)

(73) Assignee: Fujitsu Ten Limited, Kobe (JP)

( * ) Notice: Subject to any disclaimer, the term of this patent is extended or adjusted under 35 U.S.C. 154(b) by 75 days.

(21) Appl. No.: 10/067,345

(22) Filed: Feb. 7, 2002

(65) Prior Publication Data
US 2002/0105456 A1 Aug. 8, 2002

(30) Foreign Application Priority Data

| Feb. 8, 2001 | (JP) | 2001-032996 |
| Feb. 9, 2001 | (JP) | 2001-034406 |
| Feb. 9, 2001 | (JP) | 2001-034725 |

(51) Int. Cl.[7] ............................ G01S 7/40; G01S 13/93
(52) U.S. Cl. ...................... 342/174; 342/70; 342/74; 342/75; 342/165; 342/173; 342/175; 342/195
(58) Field of Search ............................. 180/167–169; 342/1–20, 73–103, 118, 128–147, 188–197, 165–174, 175, 70, 71, 72

(56) References Cited

U.S. PATENT DOCUMENTS

| 2,505,525 A | * | 4/1950 | Clapp et al. ............... 342/172 |
| 2,781,511 A | * | 2/1957 | Pear, Jr. .................... 342/172 |
| 2,802,207 A | * | 8/1957 | Sommers, Jr. et al. ...... 342/174 |

(Continued)

FOREIGN PATENT DOCUMENTS

| CH | 355485 A | 7/1961 |
| DE | 197 07 591 C1 | 10/1998 |
| EP | 0 905 526 A1 | 3/1999 |
| GB | 691570 A | 5/1953 |
| GB | 1085071 A | 9/1967 |
| GB | 2 318 010 A | 4/1998 |
| JP | U-06-47884 | 6/1994 |
| JP | A-08-327722 | 12/1996 |
| JP | A-09-178856 | 7/1997 |
| JP | 09-311186 | 12/1997 |
| JP | A-09-311186 | 12/1997 |
| JP | A-09-318731 | 12/1997 |
| JP | A-11-194165 | 7/1999 |
| JP | 11-194165 | 7/1999 |
| JP | A-11-326491 | 11/1999 |
| JP | A-2001-13238 | 1/2001 |
| WO | WO 98/38691 A1 | 9/1998 |
| WO | WO 99/50686 A1 | 10/1999 |

OTHER PUBLICATIONS

Grace, M; Abou–Jaoude, R; Noujeim, K; Bradley, D: *76GHz Radar Antenna Alignment System*, 30TH European Microwave Conference, Paris 2000, p. 175–178.

*Primary Examiner*—Bernarr E. Gregory
(74) *Attorney, Agent, or Firm*—Oliff & Berridge, PLC

(57) ABSTRACT

A radar mount direction alignment device to be used for aligning the transmit/receive direction of a radar device 2D mounted on a member on which a radar device is to be mounted, such as a vehicle 1. The radar mount direction alignment device has receiving sections b9, b10 for receiving a signal emitted from the radar device 2D, and transmission sections a9, a10 for transmitting a signal to the radar device 2D. The radar mount direction alignment device has the function of emitting, toward the radar device 2D, a signal which, upon receipt of a signal output from the radar device 2D, behaves as if having been received at and reflected from a position farther from the radar device 2D than a distance between the radar device 2D and the radar mount direction alignment device.

43 Claims, 28 Drawing Sheets

U.S. PATENT DOCUMENTS

| | | | | |
|---|---|---|---|---|
| 2,825,058 A | * | 2/1958 | Rustad et al. | 342/172 |
| 2,841,785 A | * | 7/1958 | Cunningham, Jr. et al. | 342/172 |
| 2,922,157 A | * | 1/1960 | McShan | 342/171 |
| 2,942,257 A | * | 6/1960 | Huntington | 342/165 |
| 2,952,848 A | * | 9/1960 | Zahalka et al. | 342/172 |
| 3,018,478 A | * | 1/1962 | Skillman et al. | 342/171 |
| 3,162,854 A | * | 12/1964 | Campbell | 342/171 |
| 3,199,107 A | * | 8/1965 | Mills | 342/170 |
| 3,329,953 A | * | 7/1967 | Adams et al. | 342/171 |
| 4,319,247 A | * | 3/1982 | Warren | 342/171 |
| 4,661,818 A | * | 4/1987 | Riffiod et al. | 342/172 |
| 4,679,049 A | * | 7/1987 | Riffiod | 342/172 |
| 4,683,473 A | * | 7/1987 | Haugland | 342/172 |
| 4,737,792 A | * | 4/1988 | Grone | 342/169 |
| 5,164,734 A | * | 11/1992 | Fredericks et al. | 342/172 |
| 5,177,488 A | * | 1/1993 | Wang et al. | 342/167 |
| 5,223,840 A | * | 6/1993 | Cronyn | 342/170 |
| 5,262,787 A | * | 11/1993 | Wilson et al. | 342/173 |
| 5,457,463 A | * | 10/1995 | Vencel et al. | 342/169 |
| 5,518,400 A | * | 5/1996 | Otoide et al. | 342/169 |
| 5,920,281 A | * | 7/1999 | Grace | 342/165 |
| 5,977,906 A | * | 11/1999 | Ameen et al. | 342/174 |
| 6,087,995 A | * | 7/2000 | Grace et al. | 342/174 |
| 6,329,952 B1 | * | 12/2001 | Grace | 342/174 |
| 6,335,705 B1 | * | 1/2002 | Grace et al. | 342/174 |
| 6,437,731 B1 | * | 8/2002 | Henrio et al. | 342/165 |

* cited by examiner

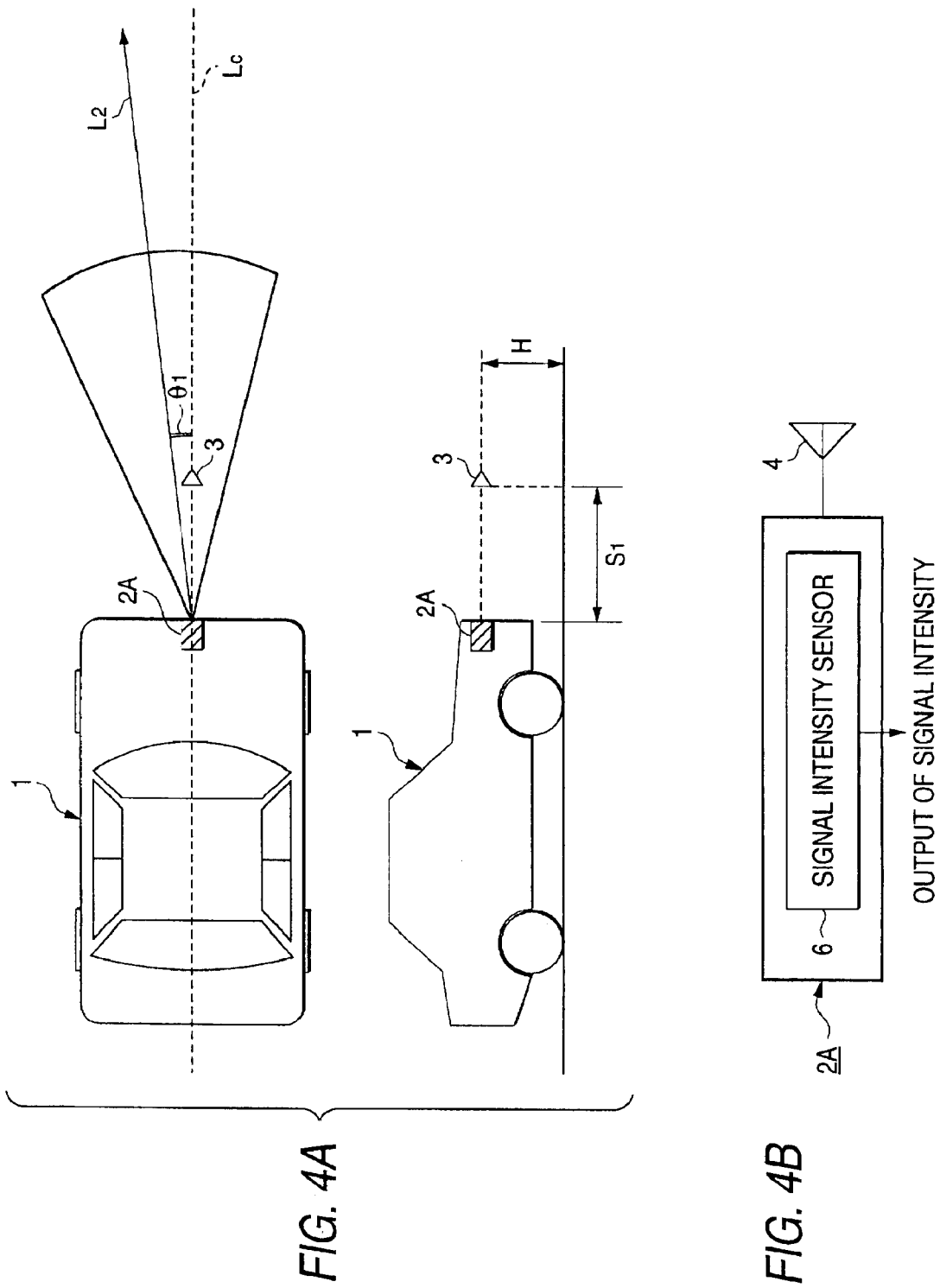

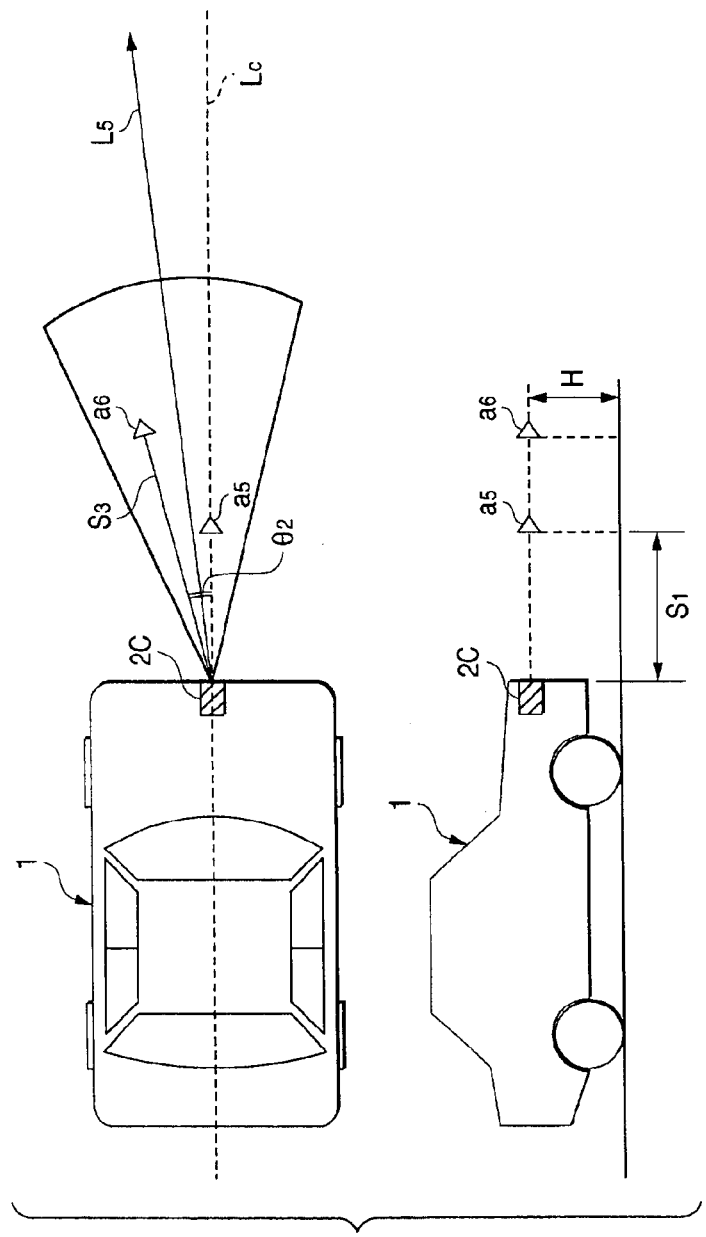
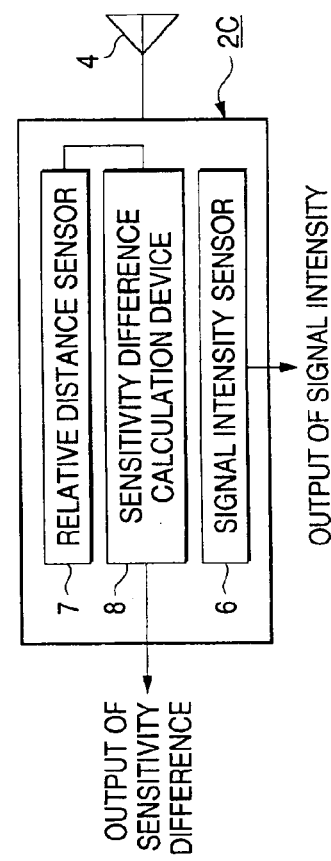
FIG. 8A
FIG. 8B

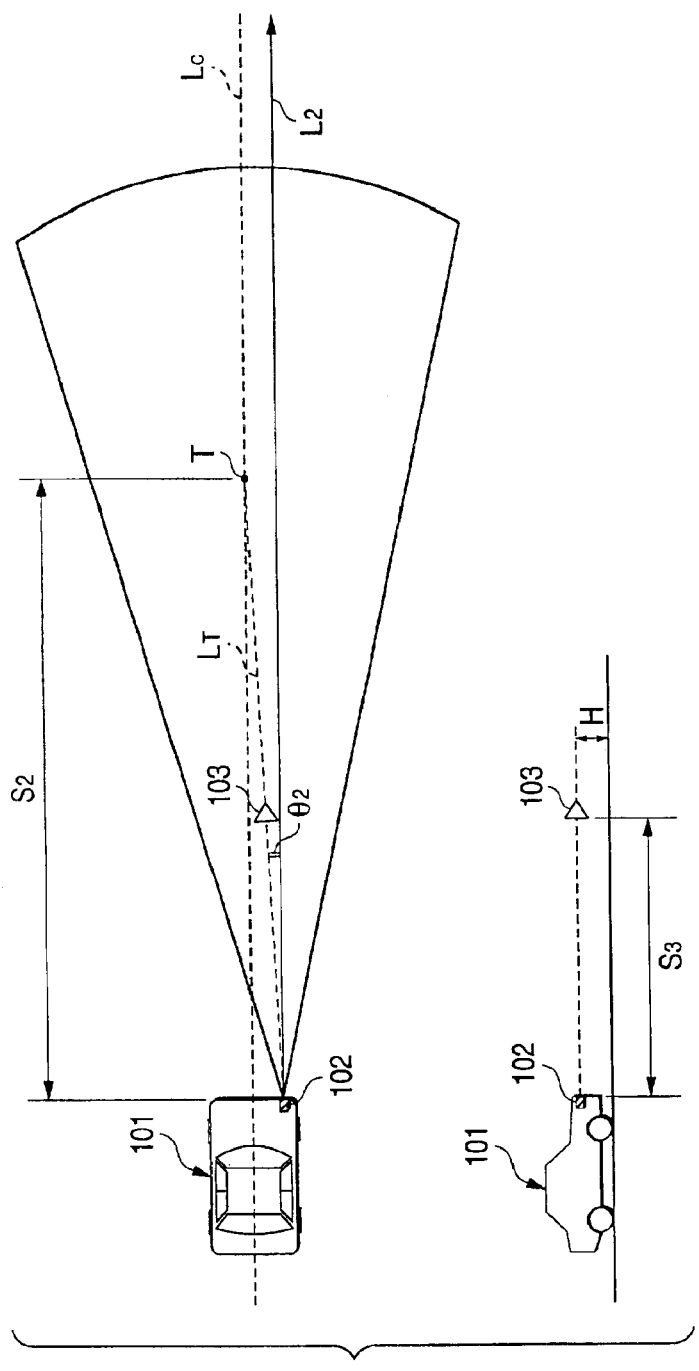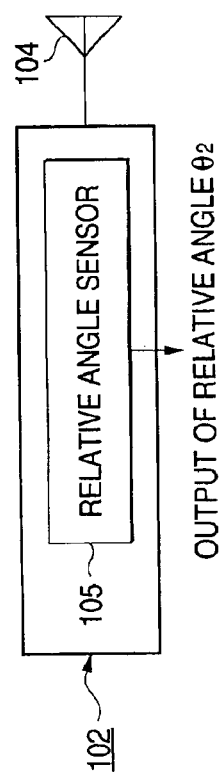
FIG. 17A
FIG. 17B

METHOD AND DEVICE FOR ALIGNING RADAR MOUNT DIRECTION, AND RADAR ALIGNED BY THE METHOD OR DEVICE

BACKGROUND OF THE INVENTION

1. Field of the Invention

The present invention relates to a method and device for aligning a radar (radio detecting and ranging device) mount direction, and to a radar system. More specifically, the present invention relates to a radar device which enables easy and correct alignment of a radar mount direction and a transmission/receipt direction to be used for aligning the transmit/receive direction of the radar, as well as to a method of aligning a radar mount direction to be used for aligning the transmit/receive direction of the radar.

2. Description of the Related Art

An intervehicle distance warning system or adaptive cruise control, which employs a radar, has already been available as a driving support system. Some inter-vehicle warning systems determine a distance between vehicles from a time lag from the time a laser pulse is emitted forward until the time of receipt of the pulse having been transmitted from a reflector of a vehicle driving ahead (i.e., a reflection plate provided on a tail lamp of a vehicle). In this way, application of a radar technology and provision of a radar on a vehicle enable realization of a superior driving support system.

However, the following problem is encountered in mounting a radar device on a vehicle. For instance, when a radar is mounted on a vehicle as an inter-vehicle distance warning system, a radar device must be mounted so as to be able to capture the vehicle driving ahead without fail.

If the transmit/receive direction of the radar is aligned with an error of 0.8 degrees, the error is equivalent to a distance of 1.4 m in a case where the vehicle is driving ahead at a distance of about 100 m. Even when another vehicle is driving ahead of a vehicle equipped with an inter-vehicle distance warning system, a sensing area of the system may deviate from a traffic lane, thereby failing to capture the vehicle ahead or misidentify a vehicle driving on the opposite lane as a vehicle driving head of oneself.

SUMMARY OF THE INVENTION

The present invention has been conceived in light of the foregoing problem and aims at providing a radar mount direction alignment device to be used for accurately aligning the transmit/receive direction of a radar device when the radar device is mounted on a vehicle or the like; a radar device which enables accurate alignment of a transmit/receive direction; and a radar mount direction alignment method for accurately aligning the transmit/receive direction of a radar device.

As a radar mount direction alignment method for accurately aligning the transmit/receive direction of a radar device, the present invention effects alignment of the transmit/receive direction of a radar device by means of placing reflection targets at predetermined locations and utilizing signals reflected from the reflection targets.

An ordinary radar device; for example, a radar device of FM-CW mode, involves noise components stemming from the radar itself, or limitations are imposed on the resolving power of a measurement section of the radar. In relation to a radar device of pulse mode, limitations are imposed on pulse width. Hence, the pulse-mode radar encounters difficulty in measuring a target disposed at short range. For these reasons, the related-art alignment method involves a necessity for ensuring a wide alignment space.

To achieve the objects, the present invention is characterized in providing a radar mount direction alignment device (1) to be used for aligning the transmit/receive direction of a radar device mounted on a member on which the radar device to be mounted, such as a vehicle, the device comprising: a receiving section for receiving a signal emitted from the radar device; a transmission section for transmitting a signal to the radar device; and a first function of transmitting, toward the radar device, a signal which, when the signal emitted from the radar device is received, behaves as if having been reflected from a reflection target disposed at a position located farther from the radar device than a distance between the radar device and the radar mount direction alignment device (1).

Upon receipt of a signal emitted from the radar device, the radar mount direction alignment device (1) transmits, toward the radar device, a signal which behaves as if having been received at and reflected from a position farther from then radar device than a distance between the radar device and the radar mount direction alignment device (1). Even when the receiving section and the transmission section are disposed close to the radar device, the radar can accurately detect the signal transmitted from the transmission section. Hence, the radar device can be aligned in a narrow space.

The present invention is also characterized in providing a radar mount direction alignment device (2) to be used for aligning the transmit/receive direction of a radar device mounted on a member on which the radar device to be mounted, such as a vehicle, the device comprising: a second function of transmitting, toward the radar device, a signal which, when the signal emitted from the radar device is received, behaves as if having been reflected from a reflection target disposed at a position farther from the radar device than a distance between the radar device and the radar mount direction alignment device (2), with a predetermined delay time.

Upon receipt of a signal emitted from the radar device, the radar mount direction alignment device (2) transmits a signal toward the radar device with a predetermined delay time. Even when the receiving section and the transmission section are disposed close to the radar device, the radar can accurately detect the signal transmitted from the transmission section. Hence, the radar device can be aligned in a narrow space.

A radar mount direction alignment device (3) consists of the radar mount direction alignment device (1) or (2), and is characterized by further comprising a transmission line for transmitting a signal, wherein a predetermined signal is transmitted toward the radar device after a received signal has been transmitted over the transmission line.

A radar mount direction alignment device (4) consists of the radar mount direction alignment device (3), and is characterized by a structure in which the transmission line is any one of the group comprising a waveguide, a dielectric line, and an optical fiber.

The radar mount direction alignment device (3) or (4) is constructed so as to transmit the predetermined signal toward the radar device after having transmitted a received signal over the transmission line. Hence, the radar mount direction alignment device can transmit a signal which behaves as if having been reflected from a position farther from the radar device than a distance between the radar device and the radar direction alignment device, or can transmit a signal toward the radar device with a delay time. For example, the transmission line includes a waveguide, a dielectric line, and an optical fiber.

A radar mount direction alignment device (5) consists of the radar mount direction alignment device (3) or (4), and is characterized by further comprising a reflector which reflects, at the other end of the transmission line, a signal having entered from one end of the transmission line, wherein the reflected signal exits from the one end of the transmission line.

A radar mount direction alignment device (6) consists of the radar mount direction alignment device (5), and is characterized by having a structure in which an antenna or lens is disposed in an entrance of the transmission line.

The radar mount direction alignment device (5) or (6) is constructed to cause a signal that is to be transmitted toward the radar device to exit from the same position in the transmission line where the signal transmitted from the radar device has entered the transmission line. More specifically, the transmission line is used for causing a signal to make a round trip. Hence, the transmission line can be utilized effectively.

Further, according to the radar mount direction alignment device (6), an antenna or lens is disposed at the entrance (or exit) of the transmission line. Hence, the signal emitted from the radar can be received with superior sensitivity or can be efficiently transmitted to the outside.

A radar mount direction alignment device (7) consists of the radar mount direction alignment device (3) or (4), and is characterized by having a structure in which the signal having entered from one end of the transmission line exits from the other end of the transmission line.

The radar mount direction alignment device according to the radar mount direction alignment device (7) is characterized by having a construction in which an antenna or lens is disposed at an entrance and/or exit of the transmission line.

The radar mount direction alignment device (7) or (8) is constructed such that the signal having entered from one end of the transmission line exits from the other end of the transmission line. Hence, there is obviated a necessity for use of the reflector used in the radar mount direction alignment device (5). Accordingly, a drop in the level of the signal in the alignment device can be suppressed. Moreover, in the radar mount direction alignment device (8), an antenna or lens is disposed in the entrance and/or exit of the transmission line. Hence, the alignment device can receive the signal emitted from the radar with superior sensitivity and can efficiently transmit a signal to the outside.

A radar mount direction alignment device (9) consists of any one of the radar mount direction alignment devices (1) through (8), and is characterized by further comprising an amplifier for amplifying a received signal.

The radar mount direction alignment device (9) is equipped with the amplifier for amplifying a received signal. Hence, an attempt can be made to recover a drop in the level of a signal which would arise during the course of traveling through the transmission line.

The radar mount direction alignment device (10) consists of any one of the radar mount direction alignment devices (1) through (9), and is characterized by further comprising a branching device for branching a received signal into a plurality of signals, wherein respective signals into which the received signal has been branched are transmitted toward the radar device.

A radar mount direction alignment device (11) consists of the radar mount direction alignment device (10), and is characterized by having a structure in which, when the radar mount direction alignment device has the amplifier, the amplifier is disposed upstream of the branching device.

In the radar mount direction alignment device (10) or (11), a plurality of transmission sections for transmitting signals toward the radar device are provided. However, commonality of a receiving section has been achieved. Hence, a difference between the signals transmitted from the transmission sections lies in only the length of a transmission line and locations of the transmission sections. Hence, more accurate alignment of the radar mount direction can be effected.

In the radar mount direction alignment device (11), the amplifier is disposed upstream of the branching device. Before a received signal is branched, the level of the signal is amplified. Hence, the level of a received signal can be amplified with extremely high efficiency.

The present invention is also characterized by providing a radar mount direction alignment method (1) which adopts any one of the radar mount direction alignment devices (1) through (8) and aligns a transmit/receive direction of a radar device, the device being mounted on a member on which a radar unit is to be mounted, such as a vehicle, and having a relative angle sensor for sensing a relative angle with reference to a target, wherein the transmission section is disposed at a predetermined position, and the transmit/receive direction of the radar device is aligned in accordance with an angle relative to the transmission section detected by the relative angle sensor and an angle relative to the receiving section detected by the relative angle sensor.

According to the radar mount direction alignment method (1), the transmission section is placed at the predetermined location (e.g., a position spaced tens of centimeters from the member on which a radar device is to be mounted). The transmit/receive direction of the radar device is aligned in accordance with an angle relative to the transmission section detected by the relative angle sensor (i.e., the angle of the transmission section relative to the radar device). For instance, the transmit/receive direction of the radar device is aligned such that angle of the transmission section relative to the radar device assumes a predetermined angle (e.g., 0 degree). Hence, the mount direction of the radar device can be aligned accurately.

The method of aligning a radar mount direction alignment method (2) according to the radar mount direction alignment method (1) is characterized in that a plurality of radar mount direction alignment devices are adopted, and a plurality of transmission sections are disposed at different positions.

According to the radar mount direction alignment method (2), the plurality of transmission sections are disposed at different positions. For instance, the transmit/receive direction of the radar device is aligned such that a difference between the elevation angles of two different transmission sections assumes a predetermined angular difference. Hence, the mount direction of the radar device can be aligned accurately.

The present invention is also characterized by providing a radar mount direction alignment method (3) which adopts any one of the radar mount direction alignment devices (1) through (8) and aligns a transmit/receive direction of a radar device, the device being mounted on a member on which a radar unit is to be mounted, such as a vehicle, and having a signal intensity sensor for receiving a signal reflected from a target and detecting the intensity of the receiving signal, wherein the transmission section is placed at a predetermined position, and a transmit/receive direction of the radar device is aligned in accordance with the intensity of a signal transmitted from the transmission section, the intensity being detected by the signal intensity sensor.

According to the radar mount direction alignment method (3), the transmission section (i.e., the radar mount direction alignment device) is provided at the predetermined location (e.g., a position spaced tens of centimeters from the member on which the radar device is to be mounted). The transmit/receive direction of the radar device is aligned in accordance with the intensity of a signal transmitted from the transmission section, the intensity being detected by the signal intensity sensor. For instance, the transmit/receive direction of the radar device is aligned such that the signal transmitted from the transmission section assumes predetermined intensity (e.g., the maximum intensity). Hence, the mount direction of the radar device can be aligned accurately.

A radar mount direction alignment method (4) consists of the radar mount direction alignment method (3), and is characterized in that a plurality of radar mount direction alignment devices are adopted, and a plurality of transmission sections are placed at different positions.

According to the radar mount direction alignment method (4), the plurality of transmission sections are placed at different positions. For instance, the transmit/receive direction of the radar device is aligned such that a difference between the intensity of signals transmitted from two different transmission sections assumes a predetermined intensity difference. Hence, the mount direction of the radar device can be aligned accurately.

The present invention is also characterized by providing a radar mount direction alignment method which adopts either one of the radar mount direction alignment devices (10) and (11) and aligns a transmit/receive direction of a radar device, the device being mounted on a member on which a radar unit is to be mounted, such as a vehicle, and having a signal intensity sensor for detecting the intensity of a signal received from the outside, wherein transmission sections for transmitting branched signals are placed at different, predetermined positions, and a transmit/receive direction of the radar device is aligned in accordance with the intensity of signals transmitted from the transmission sections, the intensity being detected by the signal intensity sensor.

According to a radar mount direction alignment method (5), the transmission sections for transmitting branched signals are placed at different, predetermined positions. For instance, the transmit/receive direction of the radar device is aligned such that a difference between the intensity of signals transmitted from two different transmission sections assumes a predetermined intensity difference. Hence, the mount direction of the radar device can be aligned accurately.

A radar mount direction alignment method (6) consists of the radar mount direction alignment method (4) or (5), and is characterized in that the transmit/receive direction of the radar device is aligned in consideration of a difference in sensitivity in detection of the intensity of signals output from the transmission sections which are susceptible to the influence of distance.

A radar mount direction alignment method (7) consists of the radar mount direction alignment method (6), and is characterized in that, when the radar device is equipped with a relative distance sensor for detecting a distance relative to a target, there is utilized the sensitivity difference determined on the basis of a relative distance detected by the relative distance sensor.

A radar mount direction alignment method (8) consists of the radar mount direction alignment method (6) or (7), and is characterized by utilizing the sensitivity difference that has been determined on the basis of information about a sensitivity difference which has been measured beforehand and corresponds to a distance relative to the target.

According to the radar mount direction alignment method (4) or (5), alignment is performed such that a difference between the intensity of signals transmitted from two difference transmission sections assumes a predetermined intensity difference, thereby aligning the transmit/receive direction of the radar device. At this time, the signals transmitted sections must be prevented from exerting influence on each other.

For example, signals of different frequencies (or receiving timings) must be used so that the radar device can separate signals from the two transmission sections. To this end, the distances of the transmission sections from the radar device must be made different. However, if the distances of the transmission sections from the radar device are made different, the difference affects the sensitivity of the radar device for detecting the intensity of the signals. The signal transmitted from a long distance becomes lower in intensity than that transmitted from a short distance.

According to any one of the radar mount direction alignment methods (6) through (8), a difference in sensitivity for detection of the intensity of signals transmitted from the transmission sections is taken into consideration. For instance, even when a plurality of transmission sections for transmitting signals which behave as if having been produced as a result of receipt of a signal from the radar device are placed at positions of different distances from the radar device, the transmit/receive direction of the radar device can be aligned accurately.

When the radar device is equipped with a relative distance sensor for detecting a distance relative to a target, alignment of the radar mount direction can be performed appropriately by means of utilizing the difference in sensitivity that has been determined in accordance with a relative distance detected by the relative distance sensor or the difference in sensitivity that has been determined on the basis of information about a difference in sensitivity corresponding to a distance relative to the target.

The present invention is also characterized by providing a radar mount direction alignment method (9) for aligning a transmit/receive direction of a radar device, the device being mounted on a member on which a radar unit is to be mounted, such as a vehicle, and having a sensor for detecting a target, wherein a reflection target is disposed at a predetermined location, and the transmit/receive direction of the radar device is aligned in accordance with information about the reflection target detected by the sensor.

According to the method aligning a mount direction of a radar (9), the reflection target is placed at the predetermined position (e.g., a position spaced 10 meters from the member on which the radar device is to be mounted). In accordance with information about the reflection target detected by the sensor (e.g., the position of the reflection target with reference to the radar device), the transmit/receive direction of the radar device is aligned.

The present invention is also characterized by providing a radar mount direction alignment method (10) for aligning a transmit/receive direction of a radar device, the device being mounted on a member on which a radar unit is to be mounted, such as a vehicle, and having a relative angle sensor for detecting a distance relative to a target, wherein a reflection target is disposed at a predetermined location, and the transmit/receive direction of the radar device is aligned in accordance with an angle relative to the reflection target detected by the relative angle sensor.

The radar mount direction alignment method (11) according to the radar mount direction alignment method (10) is characterized in that the transmit/receive direction of the radar device is aligned such that the angle relative to the target assumes a predetermined angle.

According to the method of aligning a mount direction of a radar device (10) or (11), the reflection target is placed at the predetermined position (e.g., a position spaced 10 meters from the member on which the radar device is to be mounted). In accordance with an angle relative to the reflection target detected by the relative angle sensor (i.e., the angle of the reflection target with reference to the radar device), the transmit/receive direction of the radar device is aligned. For example, the transmit/receive direction of the radar device is aligned such that the angle of the reflection target with reference to the radar device assumes a predetermined angle (e.g., 0 degree). Hence, amount direction of the radar device can be aligned accurately.

The present invention is also characterized by providing a radar mount direction alignment method (12) for aligning a transmit/receive direction of a radar device, the device being mounted on a member on which a radar unit is to be mounted, such as a vehicle, and having a reflection intensity sensor for detecting the intensity of a signal reflected from a target, wherein a reflection target is disposed at a predetermined location, and the transmit/receive direction of the radar device is aligned in accordance with the intensity of a signal reflected from the reflection target detected by the reflection intensity sensor.

A method of aligning a mount direction of a radar (13) consists of the radar mount direction alignment method (12), and is characterized in that the transmit/receive direction of the radar device is aligned such that a signal reflected from the reflection target assumes a predetermined intensity.

According to the radar mount direction alignment method (12) or (13), the reflection target is provided at the predetermined location (e.g., a position spaced 10 meters from the member on which the radar device is to be mounted). The transmit/receive direction of the radar device is aligned in accordance with the intensity of a signal reflected from the reflection target detected by the reflection intensity sensor. For instance, the transmit/receive direction of the radar device is aligned such that a signal reflected from the reflection target assumes a predetermined intensity (e.g., maximum intensity). Hence, the mount direction of the radar device can be aligned accurately.

A method of aligning a mount direction of a radar (14) consists of any one of the radar mount direction alignment methods (10) through (13), and is characterized in that the predetermined position is set on substantially a center axis in a sensing area of the radar device.

If the reflection target is placed at a position distant from the center axis of the sensing area, detection of an angle relative to the reflection target (or the intensity of a signal reflected from the reflection target) becomes difficult. According to the method of aligning a mount direction of a radar device (14), the reflection target is placed on substantially the center axis of the sensing area. Hence, an angle relative to the reflection target (or the intensity of a signal reflected from the reflection target) can be detected without fail.

A method of aligning a mount direction of a radar (15) consists of any one of the radar mount direction alignment methods (10) through (14), and is characterized in that the predetermined position is set on substantially a line connecting the location of the target for alignment with a position at which the radar device is to be mounted.

According to the radar mount direction alignment method (15), the reflection target is placed on substantially a line connecting the location of the target for alignment with a position at which the radar device is to be mounted. In accordance with the angle relative to the reflection target detected by the relative angle sensor (i.e., the angle relative to the radar device), the transmit/receive direction of the radar device is aligned.

As shown in FIG. 17A, which will be described in detail later, a reflection target 103 is provided on a line $L_T$ connecting a position T (e.g., at a position spaced 100 meters from a vehicle 101) with the mount position of the radar device 2. The mount direction of the radar device is aligned such that angle $\theta_2$ of the reflection target 103 relative to the radar device 2 (or the intensity of a signal reflected from the reflection target 103) assumes a predetermined angle (or a predetermined intensity). As a result, the radar device 102 can be mounted on the vehicle 101 so as to be able to clearly capture a vehicle driving ahead of the vehicle 101 at a distance of 100 meters.

Accordingly, even when the transmit/receive direction 102 is aligned in a limited space where position T which is a target for alignment cannot be ensured, the radar mount direction alignment method (15) enables alignment of receive/transmit direction of the radar device 102 so as to clearly capture a target (e.g., a vehicle driving ahead) located at position T which is a target for alignment.

A radar mount direction alignment method (16) consists of any one of the radar mount direction alignment methods (10) through (15), and is characterized in that, when the radar device is to be aligned in an azimuth plane, the target is provided in the azimuth plane; or that, when the radar device is to be aligned in an elevation plane, the reflection target is provided in the elevation plane.

A radar device encompasses a radar device of a type which actuates a receiving antenna provided on the radar device in an azimuth direction (i.e., within an azimuth plane) and a radar device of a type which actuates the receiving antenna provided on the radar device in an elevation direction (i.e., within an elevation plane). In a case where the receiving antenna is actuated within an azimuth plane, a radar device of such a type intensively receives a signal reflected from a target located in the same azimuth plane. When the receiving antenna is actuated within an elevation plane, the radar device intensively receives a signal reflected from a target located in the same elevation plane.

According to the method of aligning a mount direction of a radar device (16), when the radar device is aligned within an azimuth plane, the reflection target is placed in the azimuth plane. In contrast, when the radar device is aligned in the elevation plane, the reflection target is placed in the elevation plane. As a result, the radar device can receive a signal of strong reflection intensity. Hence, the mount direction of the radar device can be aligned more accurately.

A radar mount direction alignment method (17) consists of the radar mount direction alignment method (12), and is characterized in that a plurality of reflection targets are disposed at different locations.

According to the radar mount direction alignment method (17), a plurality of reflection targets are disposed at different locations. For instance, the transmit/receive direction of the radar device is aligned such that a difference between the intensity of signals transmitted from two different reflection targets assumes a predetermined intensity difference. Hence, the mount direction of the radar device can be aligned accurately.

A radar mount direction alignment method (18) consists of the radar mount direction alignment method (17), and is characterized in that the reflection targets are disposed at positions where signals reflected from the reflection targets exert no influence on each other.

According to the radar mount direction alignment method (18), the reflection targets are placed at positions where signals reflected from the reflection targets exert no influence on each other (e.g., the reflection targets are placed at different positions with reference to the radar device). Accordingly, the radar device can be aligned accurately on the basis of the signals reflected from the reflection targets.

A radar mount direction alignment method (19) consists of the radar mount direction alignment method (17) or (18), and is characterized in that the transmit/receive direction of the radar device is aligned in consideration of a difference in sensitivity for detection of the intensity of reflected signals which are susceptible to the influence of distance.

A radar mount direction alignment method (20) consists of the radar mount direction alignment method (19), and is characterized in that, when the radar device is equipped with a relative distance sensor for detecting a distance relative to a target, there is utilized the sensitivity difference determined on the basis of a relative distance detected by the relative distance sensor.

Even when two reflection targets are disposed at different positions; i.e., distances from the radar device, so as assume identical relative angles with reference to the radar device, the signal transmitted from the target disposed a short distance from the radar device is greater in intensity than that transmitted from the target disposed at a position more distant from the radar device. For these reasons, when a plurality of reflection targets are disposed and when the transmit/receive direction of the radar device is aligned, there may be a risk of use of only the intensity of signals reflected from the reflection targets resulting in a failure to accurately align the transmit/receive direction of the radar device.

According to the method of aligning a mount direction of a radar device (17) or (18), the transmit/receive direction of the radar device is aligned such that a difference in intensity of signals reflected from two different reflection targets assumes a predetermined difference level. At this time, the signals reflected from the reflection targets must be prevented from exerting influence on each other.

For instance, signals of different frequencies must be used so that the radar device can separate signals from the two reflection targets. To this end, the distances of the reflection targets from the radar device must be made different. However, if the distances of the reflection targets from the radar device are made different, the difference affects the sensitivity of the radar device for detecting the intensity of signals reflected from the reflection targets. The signal reflected from a long distance becomes lower in intensity than that reflected from a short distance. Consequently, according to either one of the radar mount direction alignment methods (19) and (20), a difference in intensity of signals reflected from the reflection targets is taken into consideration. Hence, even when a plurality of reflection targets for reflecting a signal transmitted from a radar device are placed at different positions of difference distances, the transmit/receive direction of the radar device can be aligned accurately.

When the radar device is equipped with a relative distance sensor for sensing a distance relative to a target, the mount direction of the radar device can be aligned appropriately, by means of utilizing a difference in sensitivity determined on the basis of the relative distance detected by the relative distance sensor.

The present invention is also characterized by providing a radar device (1) having a reflection sensitivity sensor for detecting the intensity of a signal reflected from a target and a relative distance sensor for detecting a distance relative to the target, the radar device comprising: a detection sensitivity difference calculation device for calculating a difference in the sensitivity in detection of the intensity of a reflected signal which is susceptible to the influence of distance, on the basis of a distance relative to the target detected by the relative distance sensor.

A radar device (2) comprises the radar device (1), and is characterized by further comprising memory for storing information about a sensitivity difference which has been determined beforehand and corresponds to a distance relative to the target, wherein the sensitivity difference calculation device determines a-difference in sensitivity for detection of intensity of a reflected signal which is susceptible to the influence of distance, on the basis of a distance relative to the target detected by the relative distance sensor and of the information stored in the memory.

The radar device (1) or (2) is provided with the reflection sensitivity sensor for detecting the intensity of a reflected signal which is susceptible to the influence of distance. When a plurality of reflection targets are placed at different positions and the transmit/receive direction of the radar device is aligned in accordance with the intensity of signals reflected from the reflection targets, the intensity being detected by the reflection intensity sensor, the sensitivity difference determined in the radar device can be utilized. Accordingly, the transmit/receive direction of the radar device can be aligned readily and accurately.

Further, the radar device (2) is provided with memory for storing information about a sensitivity difference which has been determined beforehand and corresponds to a distance relative to the target. Hence, there can be utilized the sensitivity difference which is determined on the basis of the distance relative to the target detected by the relative distance sensor and of the information stored in the memory.

The present invention is also characterized by providing a radar mount direction alignment method (21) for aligning a transmit/receive direction of a radar device which is mounted on a member on which a radar device is to be mounted, such as a vehicle, and has abeam scanning function, wherein a receiving section for receiving a signal emitted from the radar device is disposed at a predetermined position, and the transmit/receive direction of the radar device is aligned in accordance with a change in the level of a signal received by the receiving section as a result of beam scanning.

According to the method of aligning a mount direction of a radar device (21), the receiving section for receiving a signal transmitted from the radar device is placed at the predetermined location. In accordance with a change in the level of the signal received by the receiving section, the transmit/receive direction of the radar device is aligned. FIG. 24A shows an example of the relationship between a beam direction (angle) of the radar device and a directional pattern.

As is evident from FIG. 24A, if a signal transmitted from the radar device at a beam direction of 0 degree is received, the received signal assumes the maximum level. As the value of the beam direction becomes greater than 0 degree, the level of the received signal becomes smaller. Accordingly, a change in the level of a signal received by the receiving section located in the main beam direction of the radar device is primarily a large change.

As mentioned above, an intimate relationship exists between a change in the level of the signal received by the receiving section and the positional relationship between the radar device and the receiving section. Hence, the mount direction of the radar device can be aligned in accordance with a change in the level of the received signal, by means of aligning the transmit/receive direction of the radar device.

A radar mount direction alignment method (22) consists of the method of aligning a mount direction of a radar (21), and is characterized in that a signal is emitted from the radar device toward a center direction of beam scanning.

According to the method of aligning a mount direction of a radar device (22), a signal is emitted from the radar device toward a center direction of beam scanning. Hence, beam scanning is seldom wasteful, and a more characteristic change in level can be induced. For instance, provided that the receiving section A relative to the center direction (0 degree) of beam scanning of a radar device R assumes 0 degree, as shown in FIG. 24C, if a signal is emitted in the center direction of beam scanning (within only a range having an angle of 0.5 degree in opposite directions with reference to a reference of 0 degree), a change such as that shown in FIG. 25A appears in the level of a signal.

Provided that the angle of the receiving section A relative to the center direction T of beam scanning of the radar device R assumes −1.5 degrees, as shown in FIG. 24B, if a signal is emitted in the center direction of beam scanning (in only a range having an angle of 0.5 degree in opposite directions with reference to a reference of 0 degree), a change such as that shown in FIG. 25B appears in the level of a signal (here, the radar R performs scanning from left to right). Provided that the angle of the receiving section A relative to the center direction T of beams can of the radar device R assumes 1.5 degrees, as shown in FIG. 24D, if a signal is emitted in the center direction of beam scanning (within only a range having an angle of 0.5 degree in opposite directions with reference to a reference of 0 degree), a change such as that shown in FIG. 25C appears in the level of a signal. At this time, if a signal is transmitted consecutively by means of rendering a beam scan rate constant, a received signal assumes a continuous waveform, and hence stability of measurement is enhanced.

A radar mount direction alignment method (23) consists of the method of aligning a mount direction of a radar device (21) or (22), and is characterized in that the transmit/receive direction of the radar device is aligned such that the level change assumes a desired level change.

A radar mount direction alignment method (24) consists of the method of aligning a mount direction of a radar device (23), and is characterized in that the transmit/receive direction of the radar device is aligned such that the level change becomes smaller.

According to the method of aligning a mount direction of a radar device (23) or (24), the transmit/receive direction of the radar device can be aligned accurately such that a change in the level of a received signal assumes a desired level; e.g., a change in the level of a received signal becomes smaller such as that shown in FIG. 25A (a receiving level remains substantially same at any time $a_2$–$b_2$, $b_3$–$a_3$), or such that there is achieved a predetermined difference in level between the right side and the left side of signal level such as those shown in FIGS. 25B and 25C (i.e., $a_2$–$b_2$, $b_3$–$a_3$).

A radar mount direction alignment method (25) consists of any one of the methods of aligning a mount direction of a radar device (21) through (24), and is characterized in that the transmit/receive direction of the radar device is aligned with regard to a level change, through use of information about at least one end with reference to a scan direction.

According to the method of aligning a mount direction of a radar device (25), the transmit/receive direction of the radar device is aligned with regard to a level change through use of information about one end of scan direction or information about both ends of scan direction. For instance, in the case of a level change such as that shown in FIG. 25B, it is possible to ascertain whether or not alignment of transmit/receive direction of a radar device 202 based on receiving levels a2, b2 has been completed and, if the alignment has not been completed, it is possible to ascertain a direction in which or the extent to which the alignment is to be performed.

A radar mount direction alignment method (26) consists of any one of the methods of aligning a mount direction of a radar device (21) through (25), and is characterized in that the transmit/receive direction of the radar device is aligned with regard to a level change without use of information about ends of scan direction.

According to the method of aligning a mount direction of a radar device (26), a drop in the accuracy of alignment for a level change can be prevented, by means of aligning the transmit/receive direction of the radar device without use of information about the ends of scan direction, thereby preventing occurrence of a drop in the accuracy of alignment. The reason for this is that information about ends of scan direction corresponds to a signal which is received by the receiving section immediately after commencement of transmission of a signal from the radar device or a signal which is received by the receiving section immediately before transmission of a signal is ceased, both signals having the potential of immediately becoming larger or smaller.

A radar mount direction alignment method (27) consists of any one of the methods of aligning a mount direction of a radar device (21) through (26), and is characterized in that the transmit/receive direction of the radar device is aligned with regard to a level change, through use of amplitude information.

According to the method of aligning a mount direction of a radar device (27), since the amplitude information (e.g., the maximum peak value or the minimum peak value), which becomes a clear standard, is used for a level change, the transmit/receive direction of the radar device can be aligned with superior accuracy.

A radar mount direction alignment method (28) consists of any one of the methods of aligning a mount direction of a radar device (21) through (27), and is characterized in that a plurality of receiving sections are provided at different positions.

According to the method of aligning a mount direction of a radar device (28), a plurality of receiving sections are provided at different positions. Hence, the transmit/receive direction of the radar device can be aligned in accordance with a change in the level of a signal received by at least two receiving sections. Hence, the transmit/receive direction of the radar device can be aligned with higher certainty.

For example, if a failure has arisen in the radar device and beam scanning becomes impossible, no change arises in the level of a signal received by one receiving signal. Hence, the possibility of erroneous alignment is conceivable. Occurrence of such erroneous alignment can be prevented, and occurrence of a failure can be determined.

A radar mount direction alignment method (29) consists of any one of the methods of aligning a mount direction of a radar device (21) through (28), and is characterized in that an unmodulated signal is transmitted from the radar device.

According to the method of aligning a mount direction of a radar device (29), an unmodulated signal, such as a CW signal, rather than a modulated signal such as an FM-CW signal, is transmitted from the radar device. For instance, when the frequency of a signal received by the receiving section is converted into a lower frequency (e.g., an intermediate frequency), acquisition of a single intermediate frequency is facilitated. As a result, measurement of a receiving level becomes very easy.

The present invention is also characterized by providing a radar mount direction alignment device constituted of a receiving section to be used with any one of the radar mount direction alignment methods (21) through (29), the device comprising a converter for converting the frequency of a signal received by the receiving section into a lower frequency.

When a signal to be transmitted from the radar device is of high frequency, very high speed processing is required. However, the radar mount direction alignment device (12) is provided with the converter for converting the frequency of a signal received by the receiving section into a lower frequency (e.g., an intermediate frequency). Therefore, occurrence of such a problem can be prevented.

The present invention is also characterized by providing a radar mount direction alignment device constituted of a receiving section to be used with any one of the radar mount direction alignment methods (21) through (29), the device comprising a measurement instrument for measuring a receiving level from the signal received by the receiving section through use of an FFT (fast Fourier transform) system.

According to the radar mount direction alignment device (13), a receiving level at a desired time can be readily determined from waveform information or like information. Hence, the mount of the radar device can be aligned more easily in accordance with a change in the level of a received signal.

BRIEF DESCRIPTION OF THE DRAWINGS

FIG. 4A is a descriptive view for describing a method of aligning a radar mount direction according to a second embodiment of the present invention, and FIG. 4B is a block diagram schematically showing the principal section of a radar device;

FIG. 8A is a descriptive view for describing a method of aligning a radar mount direction according to a fifth embodiment of the present invention, and FIG. 8B is a block diagram schematically showing the principal section of a radar device;

FIG. 17A is a descriptive view for describing a method of aligning a radar mount direction according to a ninth embodiment of the present invention, and FIG. 17B is a block diagram schematically showing the principal section of a radar device;

DETAILED DESCRIPTION OF THE PRESENT INVENTION

Embodiments of a device and method of aligning a radar mount direction according to the present invention will be described hereinbelow by reference to the accompanying drawings.

First Embodiment

Figure 1A:
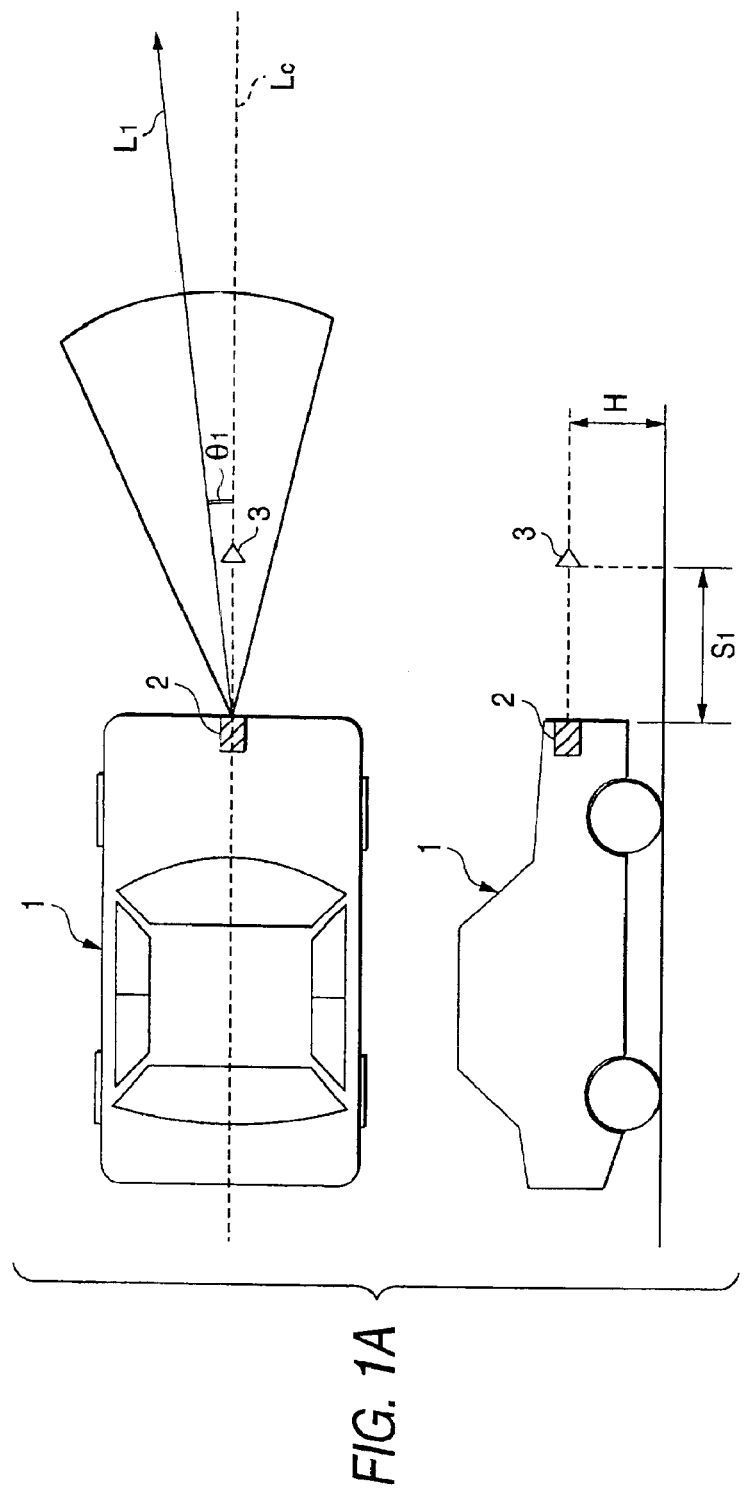
FIG. 1A is a descriptive view for describing a method of aligning a radar mount direction according to a first embodiment of the present invention.

A method of aligning a radar mount direction according to a first embodiment will now be described, by means of taking, as an example, a case where the transmit/receive direction of a radar device 2 mounted on a vehicle 1 is controlled. As shown in FIG. 1A, the radar device 2 is mounted on the front of the vehicle 1. A transmission section 3 of a radar mount direction alignment device (hereinafter also called simply "alignment device") is disposed at a position (which is a target used for aligning the mount direction of the radar device 2) spaced distance $S_1$ (e.g., tens of centimeters to one meter) from the vehicle 1.

The alignment device has the function of transmitting, toward the radar device 2, a signal which behaves as if having been transmitted from a substance farther from the radar device 2 than a distance $S_1$ or the function of sending a signal toward the radar device 2 with a predetermined delay time. The radar device 2 and the transmission section 3 are situated at a height "h" and aligned with a longitudinal center line Lc of the vehicle 1. In the drawing, $\theta_1$ denotes the angle of the transmission section 3 with reference to the center line $L_1$ of the sensing area of the radar device 2.

Figure 1B:
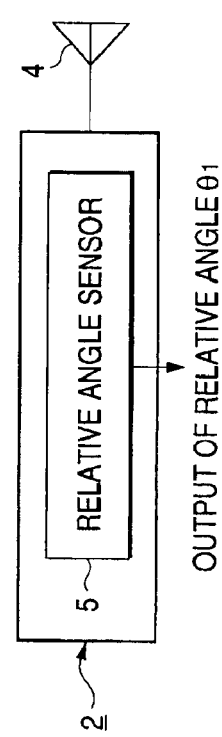
FIG. 1B is a block diagram schematically showing the principal section of a radar device.

As shown in FIG. 1B, the radar device 2 is equipped with a transmit/receive antenna 4 which rotates within a horizontal plane; and a relative angle sensor 5 for detecting a relative angle with reference to a target (i.e., an azimuth angle). Information about the angle $\theta_1$ of the transmission section 3 detected by the relative angle sensor 5 is output to the outside from the radar device 2 and is provided on a display device (not shown).

When the mount direction of the radar device 2 is aligned, the transmit/receive direction of the radar device 2 is aligned such that the angle $\theta_1$ assumes a predetermined value (e.g., 0 degree) while the angle $\theta_1$ is detected by the relative angle sensor 5.

Under the radar mount direction alignment method according to the first embodiment, the transmission section 3 is provided on the longitudinal center line Lc of the vehicle 1 and in the position spaced distance $S_1$ from the vehicle 1. The transmit/receive direction of the radar device 2 is aligned such that the angle $\theta_1$ of the transmission section 3 with reference to the radar device 2 detected by the relative angle sensor becomes a predetermined angle. Hence, the mount direction can be aligned accurately.

An ordinary radar device; for example, a radar device of FM-CW mode, involves noise components stemming from the radar itself, or limitations are imposed on the resolving power of a measurement section of the radar. In relation to a radar device of pulse mode, limitations are imposed on pulse width. Hence, the pulse-mode radar encounters difficulty in measuring a target disposed at short range. However, the alignment device has the function of sending, toward the radar device 2, a signal which behaves as if having been received at and transmitted from an object farther from the radar device 2 than distance $S_1$, or the function of sending a signal toward the radar device 2 with a predetermined period of delay time. Hence, an attempt can be made to reduce the space required for alignment.

Next will be described an adjustment device having the function of sending, toward the radar device 2, a signal which behaves as if having been received at and transmitted from an object disposed at a position farther from the radar device 2 than a distance of $S_1$, or the function of sending a signal toward the radar device 2 with a predetermined period of delay time.

Figure 2A:
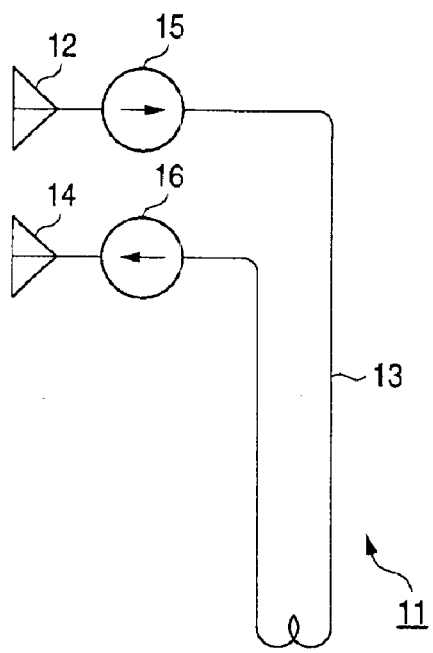
FIGS. 2A and 2B are block diagrams schematically showing the principal section of the radar mount direction alignment device according to the first embodiment.
Figure 2B:
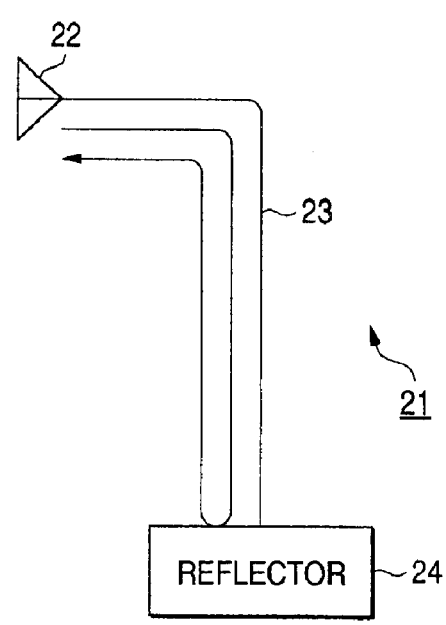

FIGS. 2A and 2B show radar mount direction alignment devices 11 and 21. The radar mount direction device 11 comprises an antenna 12 for receiving a signal transmitted from the radar device 2; a transmission line 13 for transmitting a signal; an antenna 14 for transmitting, to the radar device 2, the signal that has been transmitted over the transmission line 13; and directional couplers 15, 16. When the signal emitted from the radar device 2 is received by the antenna 12, a signal is transmitted from the antenna 14 toward the radar device 2, wherein the signal behaves as if having been received at and transmitted from a position spaced distance $S_1$ from the radar device 2, plus a distance corresponding to half the distance equivalent to a time delay determined by the length of the transmission line 13.

The radar mount direction alignment device 21 has a transmit/receive antenna 22; a transmission line 23 for transmitting a signal; and a reflector 24 connected to the transmission line 23. When the signal emitted from the radar device 2 is received by the antenna 22, a signal is transmitted from the antenna 22 toward the radar device 2, wherein the signal behaves as if having been received at and transmitted from a position spaced distance $S_1$ from the radar device 2, plus a distance corresponding to a time delay determined by the length of the transmission line 23.

Figure 3A:
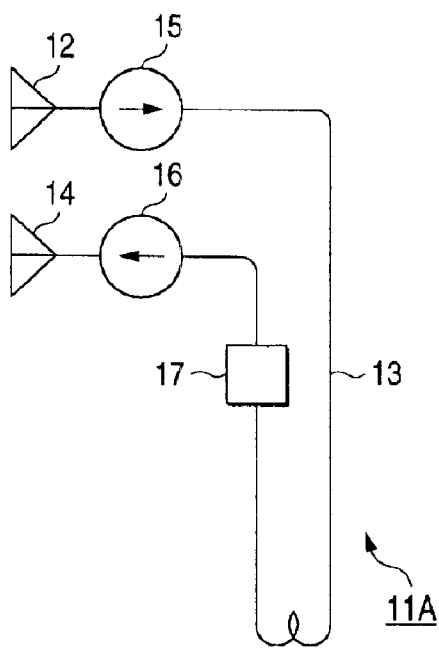
FIGS. 3A and 3B are block diagrams schematically showing the principal section of the radar mount direction alignment device according to the first embodiment.
Figure 3B:
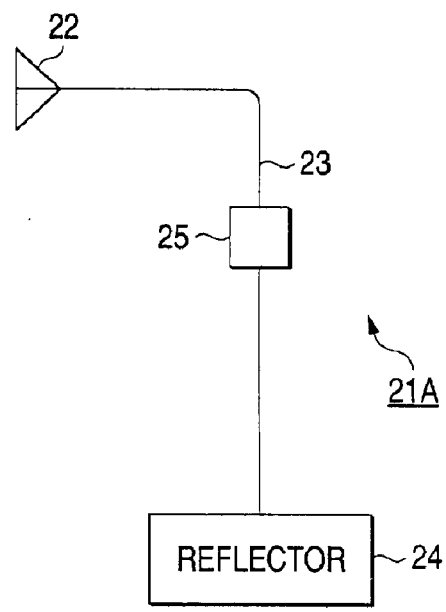

Here, the antenna 12 is provided at the entrance of the transmission line 13, and the antenna 14 is provided at the exit of the same. Further, the antenna 22 is provided at the entrance/exit of the transmission line 23. Alternatively, another member for improving the transmit/receive sensitivity, such as a lens, may be provided in lieu of the antenna. The transmission lines 13 and 23 include a waveguide, a dielectric line, and an optical fiber. As shown in FIGS. 3A and 3B, there may also be employed a radar mount direction alignment device 11A having an amplifier 17 provided in the transmission line 13, or a radar mount direction alignment device 21A having an amplifier 25 provided in the transmission line 23. Use of these devices enable recovery of a signal level which will drop in the course of the signal passing through the transmission line 13 or 23.

Second Embodiment

A method of aligning a radar mount direction according to a second embodiment of the present invention will now be described. As shown in FIG. 4A, a radar device 2A is mounted on the front of the vehicle 1. The transmission section 3 of the alignment device is disposed at a position spaced distance $S_1$ (e.g., tens of centimeters to one meter) from the vehicle 1.

The alignment device has the function of transmitting, toward the radar device 2A, a signal which behaves as if having been transmitted from further from the radar device 2A than distance $S_3$, or the function of sending a signal toward the radar device 2A with a predetermined delay time. The radar device 2A and the transmission section 3 are situated at a height "h" and aligned with a longitudinal center line Lc of the vehicle 1. In the drawing, $\theta_1$ denotes the angle of the transmission section 3 with reference to the radar device 2A.

Figure 5:
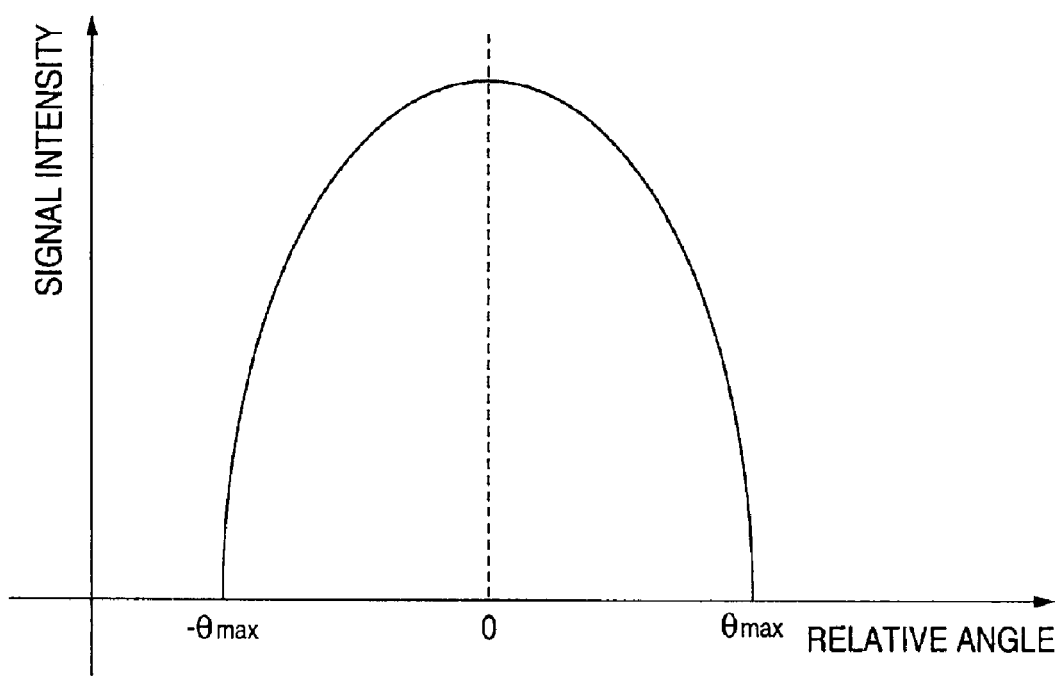
FIG. 5 is a view showing a relationship between the angle of a target with reference to a radar device and reflection intensity.

As shown in FIG. 4B, the radar device 2A is equipped with a transmit/receive antenna 4 which rotates within a horizontal plane (a stationary antenna may alternatively be employed); and a signal intensity sensor 6 for detecting the intensity of an external signal. Information about the intensity of a signal output from the transmission section 3, the intensity being detected by the signal intensity sensor 6, is output to the outside from the radar device 2A and is provided on a display device (not shown). As shown in FIG. 5, when the angle $\theta_1$ of the transmission section 3 with reference to the radar device 2A is 0 degree, the signal output from the transmission section 3 assumes the highest intensity. As the value of the angle $\theta_1$ increases, the intensity of the signal becomes smaller.

When the mount direction of the radar device 2A is aligned, the transmit/receive direction of the radar device 2A is aligned such that signal intensity attains a predetermined level (e.g., the maximum intensity) while signal intensity is detected by the signal intensity sensor 6.

Under the method for aligning a radar mount direction according to the second embodiment, the transmission section 3 is provided on the longitudinal center line Lc of the vehicle 1 and at the position spaced distance $S_1$ from the vehicle 1. The transmit/receive direction of the radar device 2A is aligned such that the intensity of the signal output from the transmission section 3, the intensity being detected by the signal intensity sensor 6, attains a predetermined level. Accordingly, a mount direction can be aligned accurately.

An ordinary radar device; for example, a radar device of FM-CW mode, involves noise components stemming from the radar itself, or limitations are imposed on the resolving power of a measurement section of the radar. In relation to a radar device of pulse mode, limitations are imposed on pulse width. Hence, the pulse-mode radar encounters difficulty in measuring a target disposed at short range. However, the alignment device has the function of sending, toward the radar device 2A, a signal which behaves as if having been received at and transmitted from a position further from the radar device 2 distant than a distance of $S_1$, or the function of sending a signal toward the radar device 2A with a predetermined period of delay time. Hence, an attempt can be made to reduce the space required for alignment.

Third Embodiment

Figure 6A:
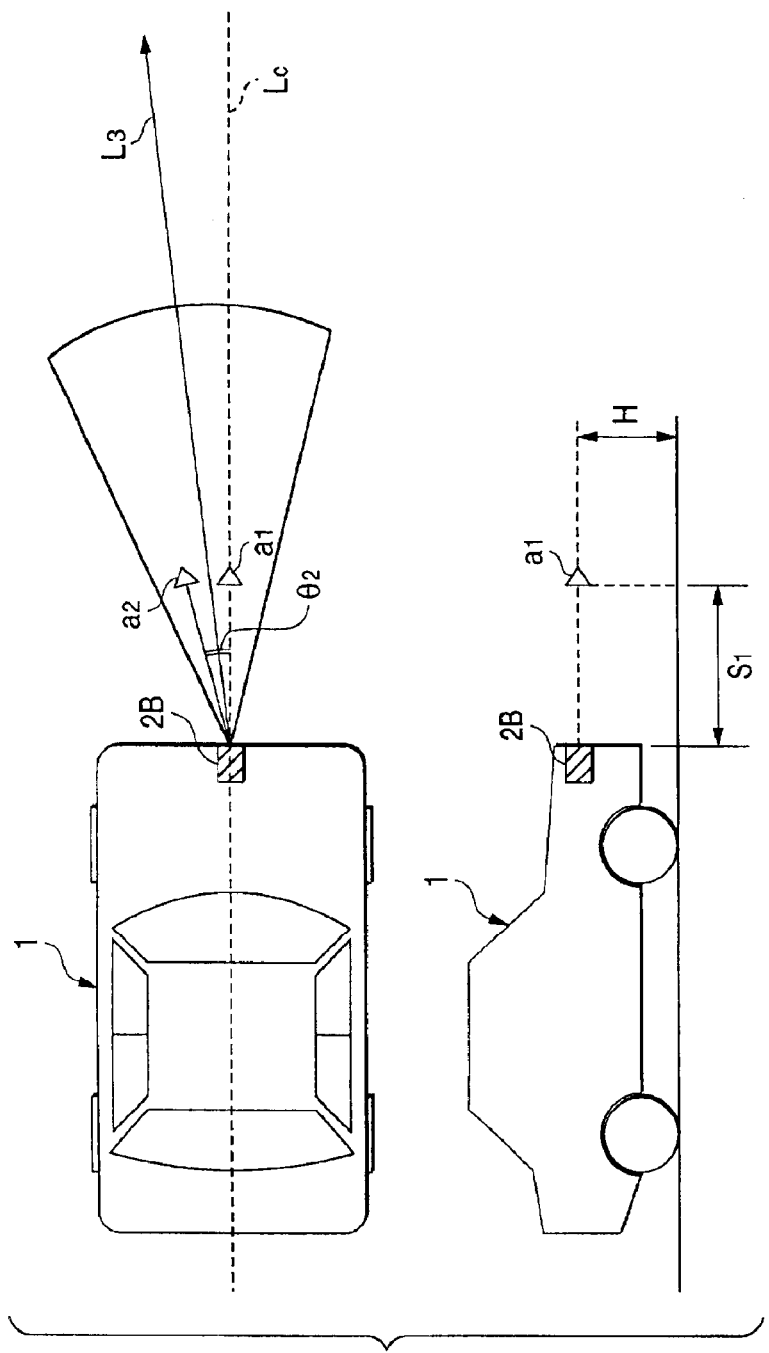
FIG. 6A is a descriptive view for describing a method of aligning a radar mount direction according to a third embodiment of the present invention.

A method of aligning a radar mount direction according to a third embodiment of the present invention will now be described. As shown in FIG. 6A, a radar device 2B is mounted on the front of the vehicle 1. Transmission sections $a_1$, $a_2$ of the alignment device are disposed at positions spaced distance $S_1$ (e.g., tens of centimeters to one meter) from the vehicle 1. Here, the transmission section $a_1$ is provided on the longitudinal center line Lc of the vehicle 1, and the transmission section $a_2$ is provided at a position offset from the center line Lc by angle $\theta_2$.

Figure 6B:
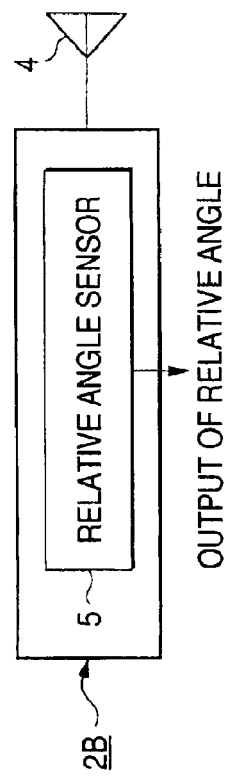
FIG. 6B is a block diagram schematically showing the principal section of a radar device.

As shown in FIG. 6B, the radar device 2B is equipped with the transmit/receive antenna 4 which rotates within a horizontal plane, and a relative angle sensor 5 for sensing a relative angle with reference to the target. Information about angles of the transmission sections $a_1$, $a_2$ detected by the relative angle sensor 5 is output to the outside from the radar device 2B. The information is then displayed on a display device (not shown).

When the mount direction of the radar device 2B is aligned, the transmit/receive direction of the radar device 2B is aligned such that the angular difference defined between the transmission sections $a_1$ and $a_2$ assumes $\theta_2$ while the relative angle is detected by the relative angle sensor 5.

So long as the transmit/receive direction of the radar device 2B is aligned such that the angular difference assumes $\theta_2$, the transmit/receive direction of the radar device 2B will be aligned such that the angle of the transmission section $a_1$ relative to the radar device 2B assumes 0 degree.

Under the method for aligning a radar mount direction according to the third embodiment, the transmission sections $a_1$, $a_2$ are disposed at different positions. The transmit/receive direction of the radar device 2B is aligned such that the angular difference defined between the transmission sections $a_1$, $a_2$ assumes a predetermined value ($\theta_2$ in this case). Hence, an accurate mount direction can be aligned.

Fourth Embodiment

Figure 7:
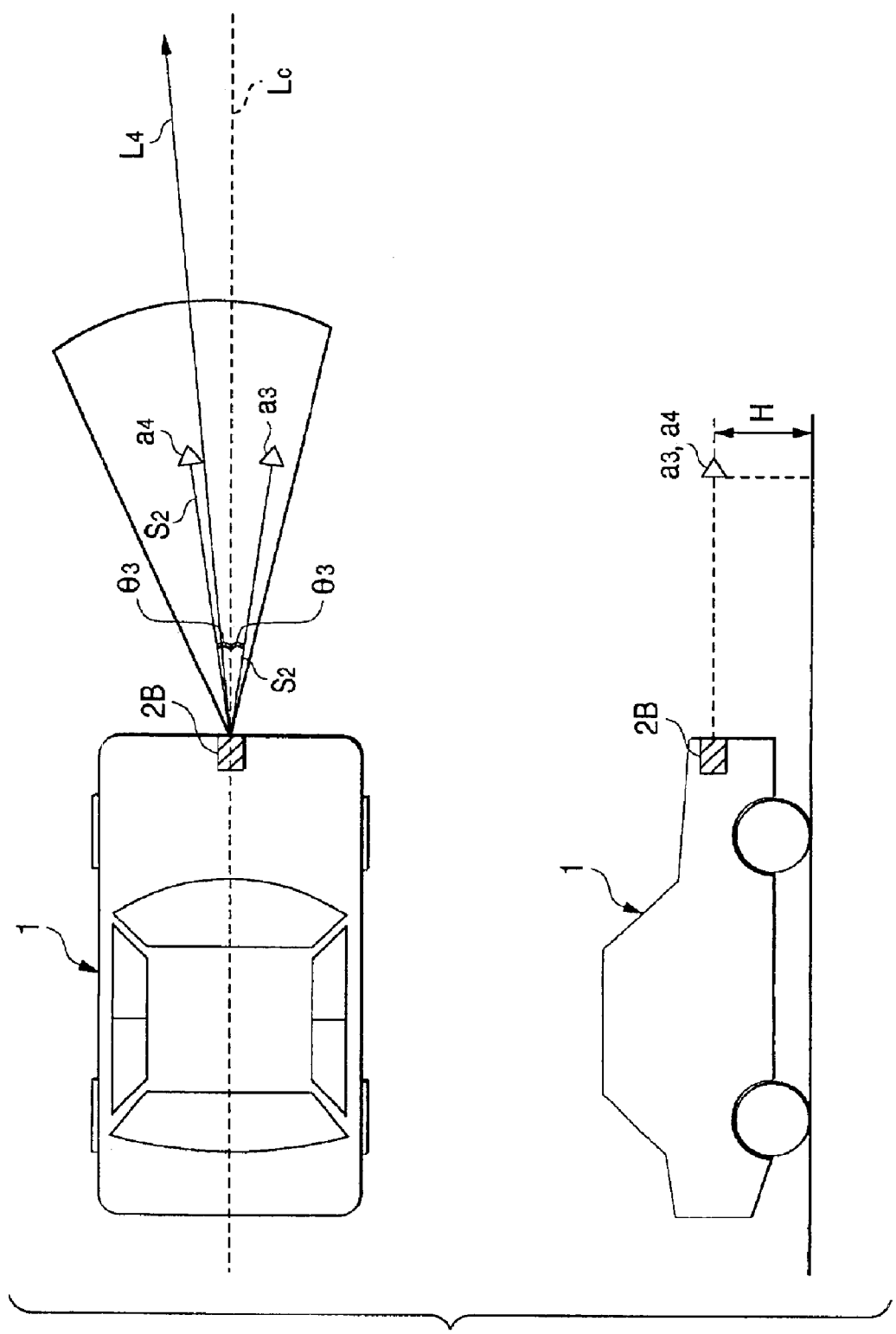
FIG. 7 is a descriptive view for describing a method of aligning a radar mount direction according to a fourth embodiment of the present invention.

A method of aligning a radar mount direction according to a fourth embodiment of the present invention will now be described. As shown in FIG. 7, the radar device 2B is mounted on the front of the vehicle 1. Transmission sections $a_3$, $a_4$ of the alignment device are disposed at positions spaced distance $S_1$ (e.g., tens of centimeters to one meter) from the vehicle 1. Here, the transmission section $a_3$ is disposed at a position offset from the longitudinal center line Lc of the vehicle 1 by angle $\theta_3$, and the transmission section $a_4$ is disposed at a position offset from the center line Lc by angle $\theta_4$.

When the mount direction of the radar device 2B is aligned, the transmit/receive direction of the radar device 2B is aligned such that the transmission section $a_3$ and the transmission section $a_4$ assume identical angles $\theta_3$ while the relative angle is being detected by the relative angle sensor 5.

So long as the transmit/receive direction of the radar device 2B is aligned such that the relative angles of the transmission sections $a_3$, $a_4$ become identical with each other, the transmit/receive direction of the radar device 2B will be aligned such that the angle of the transmission section $a_3$ relative to the radar device 2B and the angle of the transmission section $a_4$ relative to the radar device 2B assume $\theta_3$. More specifically, the transmit/receive direction of the radar device 2B is aligned such that a center line $L_4$ of the sensing area of the radar device 2B is aligned exactly with the center line Lc.

Under the method for aligning a radar mount direction according to the fourth embodiment, the transmission sections $a_3$, $a_4$ are disposed symmetrically with respect to the center line Lc. The transmit/receive direction of the radar device 2B is aligned such that the transmission sections $a_3$ and $a_4$ assume identical relative angles. Hence, an accurate mount direction can be aligned.

Fifth Embodiment

A method of aligning a radar mount direction according to a fifth embodiment of the present invention will now be described. As shown in FIG. 8A, a radar device 2C is mounted on the front of the vehicle 1. A transmission section $a_5$ of the alignment device is disposed at a position spaced distance $S_1$ (e.g., tens of centimeters to one meter) from the vehicle 1. Further, a transmission section $a_6$ of the alignment device is disposed at a position spaced distance $S_3$ (e.g., one to two meters) from the vehicle 1. The transmission section $a_5$ is provided on the longitudinal center line Lc of the vehicle 1, and the transmission section $a_6$ is provided at a position offset from the center line Lc by angle $\theta_5$.

As shown in FIG. 8B, the radar device 2C is equipped with the transmit/receive antenna 4 which rotates within a horizontal plane; the signal intensity sensor 6 for detecting the intensity of a signal reflected by a target; a relative distance sensor 7 for sensing a relative distance between the radar device 2C and the target; and a sensitivity difference calculation device 8 for determining a difference in sensitivity between the intensity of signals on the basis of the relative distance from the target detected by the relative distance sensor 7. Information about the intensity of signals reflected by the transmission sections $a_5$, $a_6$ and detected by the signal intensity sensor 6 and information about sensitivity difference are output to the outside of the radar device 2C. The information is then displayed on a display device (not shown).

Methods of determining a sensitivity difference include a method of determining a sensitivity difference using a radar equation, and a method of determining a sensitivity difference using the information stored in the memory which stores information about a sensitivity difference appropriate to a relative distance from the target.

Figure 9:
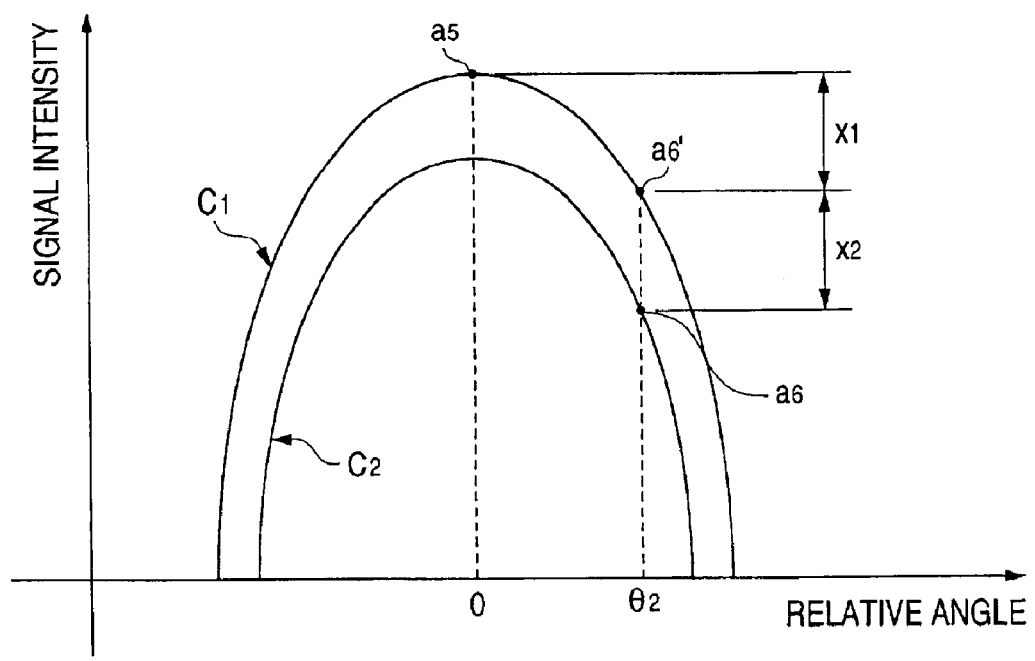
FIG. 9 is a view showing a relationship between the angle of a target with reference to a radar device and reflection intensity.

FIG. 9 shows a relationship between an angle defined between the radar device 2C and the target, and the intensity of the signal transmitted from the target. In the drawing, $C_1$ denotes the relationship between the angle of the target disposed at a position spaced from the radar device 2C by distance $S_1$ and the intensity of the signal transmitted from the target. In the drawing, $C_2$ denotes the relationship between the angle of the target disposed at a position spaced from the radar device 2C by distance $S_3$ and the intensity of the signal transmitted from the target.

As shown in FIG. 9, even when two transmission sections are disposed at different positions relative to the radar device 2C so as assume an identical relative angle with reference to the radar device 2C, the signal transmitted from an object disposed a short distance from the radar device 2C is greater in intensity than that transmitted from an object disposed at a position more distant from the radar device 2C. For instance, the angle defined between the radar device 2C and the transmission section $a_6$ and the angle defined between the radar device 2C and a transmission section $a_6$, both assume $\theta_2$. However, the signal output from the transmission section $a_6$, is greater in intensity than that output from the transmission section $a_6$ by $x_2$.

When the mount direction of the radar device 2C is aligned, the sensitivity difference calculation device 8 computes a sensitivity difference, and the intensity of signals is detected by the signal intensity sensor 6. The transmit/receive direction of the radar device 2C is aligned such that a difference between the intensity of the signal output from the transmission section $a_5$ and the intensity of the signal output from the transmission section $a_6$ that takes into account a sensitivity difference $x_2$ attains a predetermined level ($x_1$ in this case).

For instance, if the transmit/receive direction of the radar device 2C is aligned such that the intensity difference assumes a predetermined level $x_1$, the transmit/receive direction of the radar device 2C is aligned such that the angle of the transmission section $a_5$ relative to the radar device 2C assumes 0 degree, as shown in FIG. 9.

Under the method of aligning a radar mount direction according to the fifth embodiment, a difference in sensitivity between the intensity of signals which are susceptible to the influence of distance is taken into consideration. Hence, the transmission sections $a_5$, $a_6$ are disposed at appropriate positions, and the transmit/receive direction of the radar device 2C can be aligned accurately through use of the intensity of the signals output from the transmission sections $a_5$, $a_6$.

Sixth Embodiment

Figure 10:
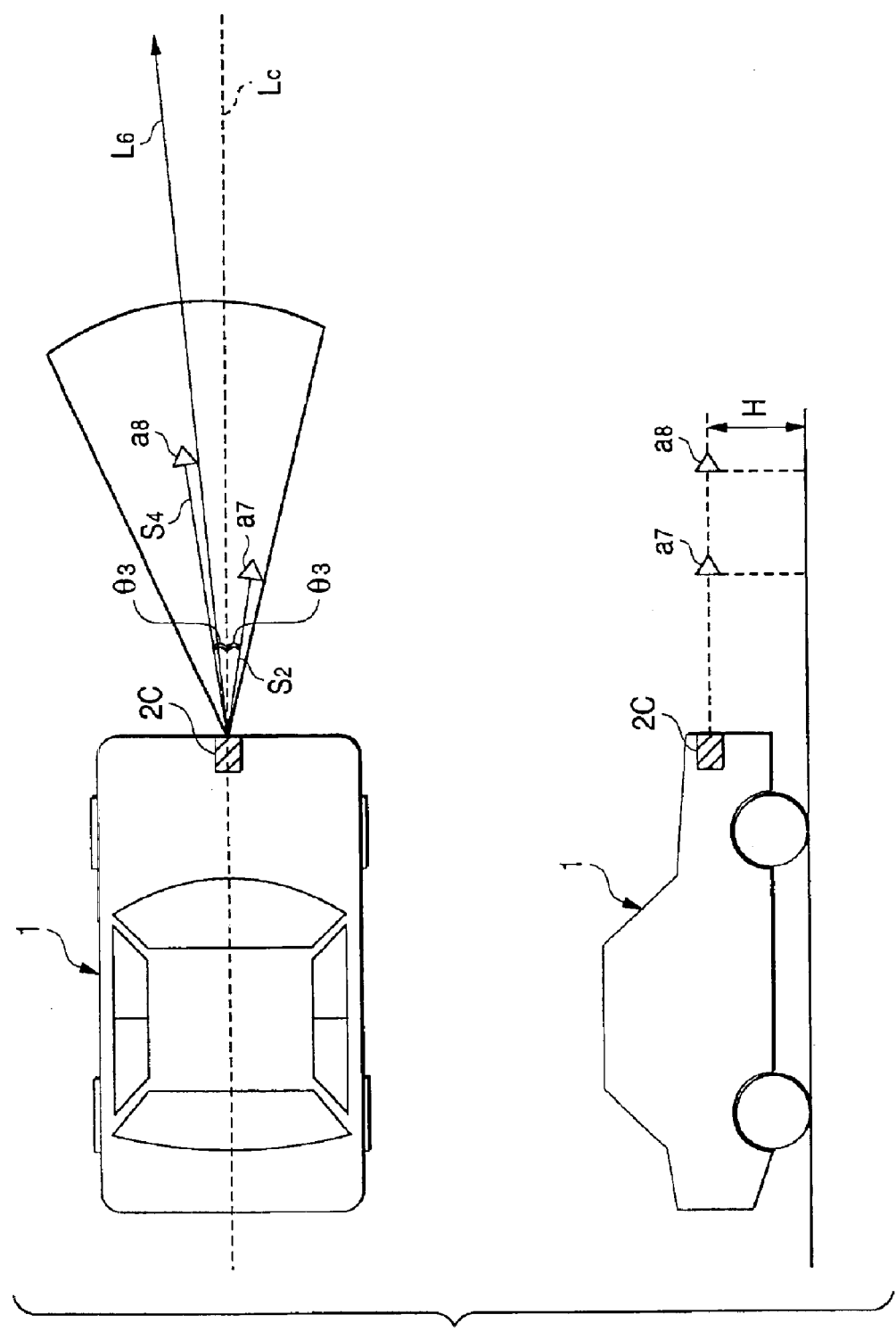
FIG. 10 is a descriptive view for describing a method of aligning a radar mount direction according to a sixth embodiment of the present invention.

A method of aligning a radar mount direction according to a sixth embodiment of the present invention will now be described. As shown in FIG. 10, the radar device 2C is mounted on the front of the vehicle 1. A transmission section $a_7$ of the alignment device is disposed at a position spaced distance $S_2$ (e.g., tens of centimeters to one meter) from the vehicle 1. Further, a transmission section $a_8$ of the alignment device is disposed at a position spaced distance $S_4$ (e.g., one meter to two meters) from the vehicle 1. Here, the transmission sections $a_7$, $a_8$ are disposed at opposite directions from the longitudinal center line Lc of the vehicle 1, by angle $\theta_3$ from the longitudinal center line.

Figure 11:
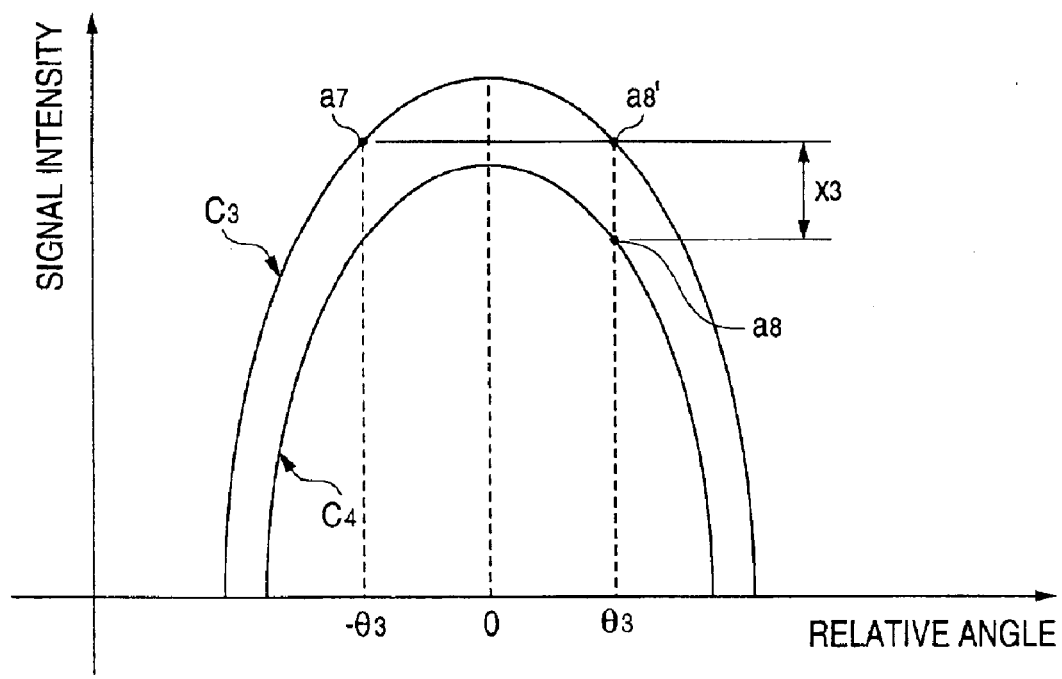
FIG. 11 is a view showing a relationship between the angle of a target with reference to a radar device and reflection intensity.

FIG. 11 shows a relationship between an angle defined between the radar device 2C and the target and the intensity of the signal transmitted from the target. In the drawing, $C_3$ denotes the relationship between the angle of the target disposed at a position spaced from the radar device 2C by distance $S_2$ and the intensity of the signal transmitted from the target. In the drawing, $C_4$ denotes the relationship between the angle of the target disposed at a position spaced from the radar device 2C by distance $S_4$ and the intensity of the signal transmitted from the target.

As shown in FIG. 11, even when two transmission sections are disposed at different positions relative to the radar device 2C so as assume identical relative angles with reference to the radar device 2C, the signal transmitted from an object disposed a short distance from the radar device 2C is greater in intensity than that transmitted from an object disposed at a position more distant from the radar device 2C. For instance, the angle defined between the radar device 2C and the transmission section $a_8$ and the angle defined between the radar device 2C and transmission sections $a_7$, $a_6$, assume identical angles $\theta_3$. However, the signals output from the transmission sections $a_7$, $a_6$, are greater in intensity than that output from the transmission sections $a_8$ by $x_3$.

When the mount direction of the radar device 2C is aligned, the sensitivity difference calculation device 8 (see FIG. 8) computes a sensitivity difference, and the intensity of signals is detected by the signal intensity sensor 6 (see FIG. 8). The transmit/receive direction of the radar device 2C is aligned such that a difference between the intensity of the signal output from the transmission section $a_7$ and the intensity of the signal output from the transmission section $a_8$ that takes into account a sensitivity difference $x_3$ disappears.

If the transmit/receive direction of the radar device 2C is aligned such that the intensity difference disappears, the transmit/receive direction of the radar device 2C is aligned such that the angle of the transmission section $a_7$ relative to the radar device 2C and the angle of the transmission section $a_8$ relative to the radar device 2C both assume $\theta_3$, as shown in FIG. 11. In other words, a center line $L_6$ of the sensing area of the radar device 2C is aligned exactly with the center line Lc.

Under the method of aligning a radar mount direction according to the sixth embodiment, a difference in sensitivity between the intensity of signals which are susceptible to the influence of distance is taken into consideration. Hence, the transmission sections $a_7$, $a_8$ are disposed at appropriate locations, and the transmit/receive direction of the radar device 2C can be aligned accurately through use of the intensity of the signals output from the transmission sections $a_7$, $a_8$.

Under the method of aligning a radar mount direction according to the fifth (or sixth) embodiment, the distance of the transmission section $a_5$ (or $a_7$) from the radar device 2C is set so as to differ from the distance of the transmission section $a_6$ (or $a_8$) from the radar device 2C so as to prevent the signal output from the transmission section $a_5$ ($a_7$) and that output from the transmission section $a_6$ ($a_8$) from exerting no influence on each other. However, under a method of aligning a radar mount direction according to another embodiment, a transmission line of the alignment device having the transmission section $a_6$ ($a_8$) may be set so as to become longer than that of the alignment device having the transmission section $a_5$ ($a_7$). As a result, an attempt can be made to reduce the space required for alignment.

Figure 12:
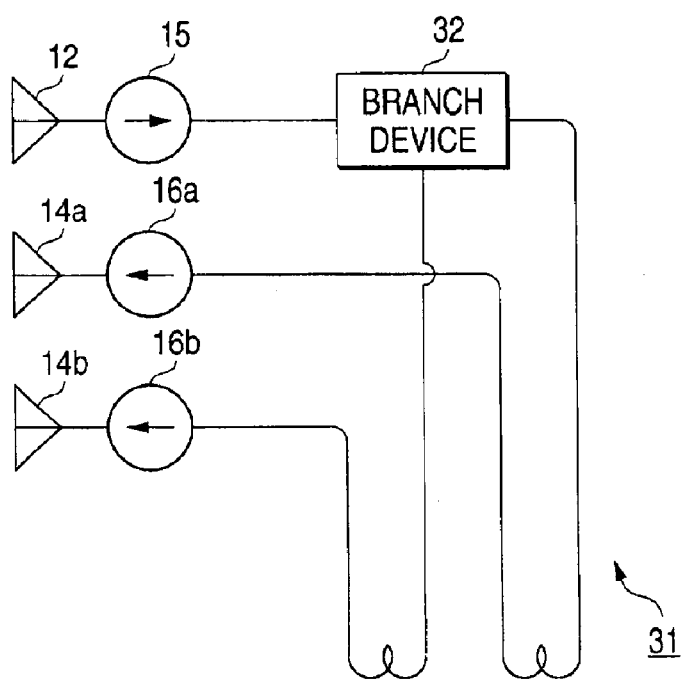
FIG. 12 is a block diagram schematically showing the principal section of the radar mount direction alignment device.
Figure 13A:
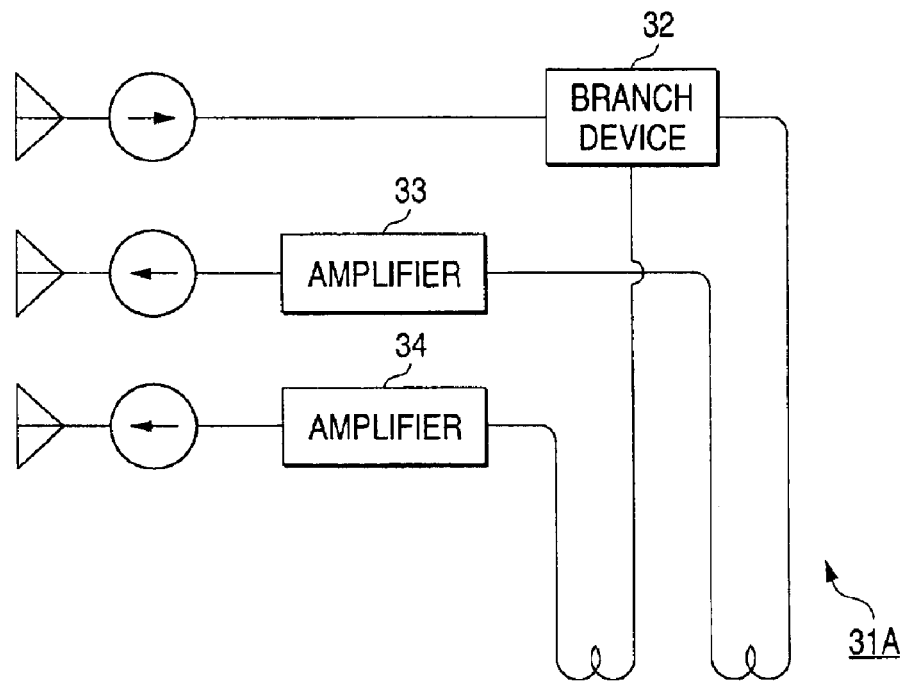
FIGS. 13A and 13B are block diagrams schematically showing the principal section of the radar mount direction alignment device.
Figure 13B:
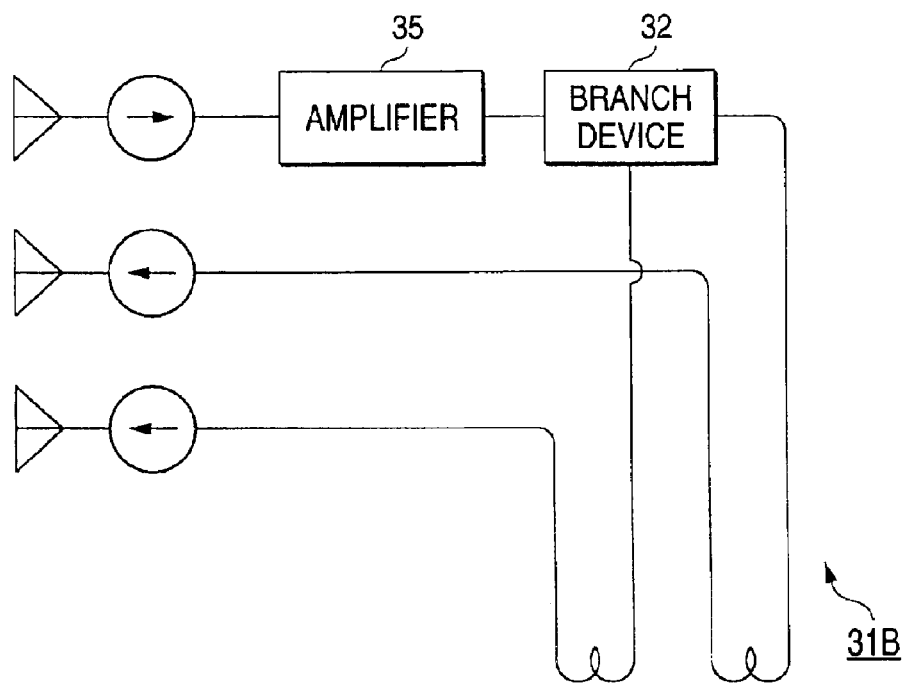

As shown in FIG. 12, when a plurality of transmission sections are disposed, there may be employed a radar mount direction alignment device 31 equipped with a branch device 32 for branching a received signal into a plurality of signals. Alternatively, as shown in FIGS. 13A and 13B, there may be employed radar mount direction alignment devices 31A, 31B having amplifiers 33 through 35 provided in transmission lines. Use of the radar mount direction alignment device 31 equipped with the branch device 32 enables sharing of the receiving section 13 even when the transmission sections 14a, 14b differ from each other. A difference between the signals transmitted from the transmission sections 14a, 14b lies in only the lengths of transmission lines and the locations where the transmission sections 14a, 14b are provided. Hence, the radar mount direction can be aligned more precisely.

Under the method of aligning a radar mount direction according to any one of the first through sixth embodiments, there is described only a case where the mount directions of the radar devices 2 and 2A through 2C are aligned within a horizontal plane. However, the radar devices 2 and 2A through 2C are provided with a transmit/receive antenna which rotates within a vertical plane. Even when the mount directions of the radar devices 2 and 2A through 2C are aligned within a vertical plane, the radar mount direction can be aligned in the same manner as described previously.

Seventh Embodiment

Figures 14A, 14B:
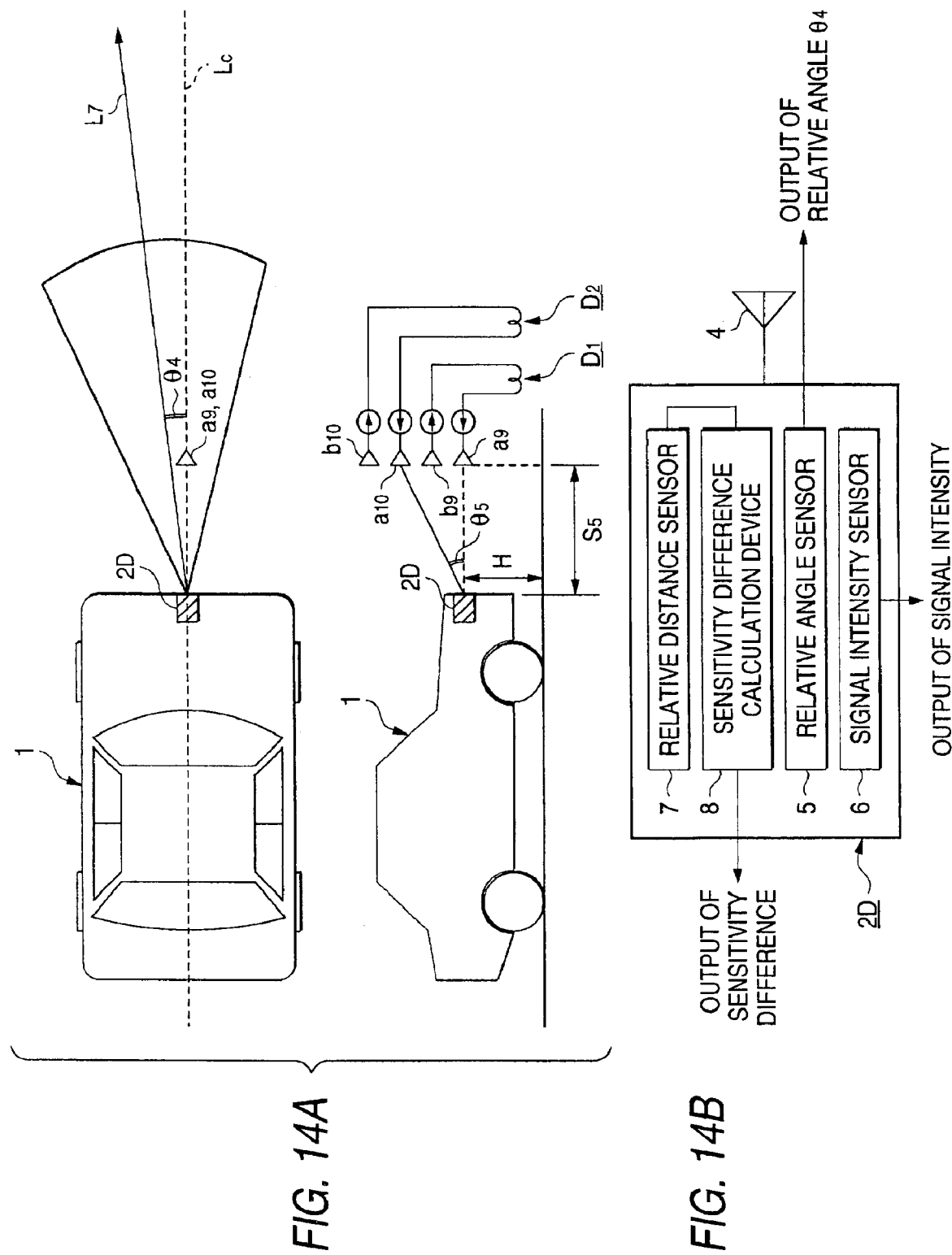
FIG. 14a is a descriptive view for describing a method of aligning a radar mount direction according to a seventh embodiment of the present invention.
FIG. 14b is a block diagram schematically showing the principal section of a radar device.

A method of aligning a radar mount direction according to a seventh embodiment of the present invention will now be described. As shown in FIG. 14A, a radar device 2D is mounted on the front of the vehicle 1. A transmission section $a_9$ and a receiving section $b_9$ of a radar mount direction alignment device $D_1$ and a transmission section $a_{10}$ and a receiving section $b_{10}$ of an alignment device $D_2$ are provided at a position spaced from the vehicle 1 by distance $S_5$ (e.g., tens of centimeter to one meter).

The alignment device $D_1$ is arranged so as to transmit, toward the radar device 2D from the transmission section $a_9$, a signal which behaves as if having been received at and transmitted from a position spaced distance $S_5$ from the radar device 2D (e.g., a position separated five meters from the radar 2D). The alignment device $D_2$ is arranged so as to transmit, toward the radar 2 from the transmission section $a_{10}$, a signal which behaves as if having been received at and transmitted from a position spaced distance $S_5$ from the radar device 2D (e.g., a position separated 10 meters from the radar 2D).

As shown in FIG. 14B, the radar device 2D is equipped with the transmit/receive antenna 4 which rotates within a horizontal plane; the relative angle sensor 5 for detecting a relative angle with reference to a target (i.e., an azimuth angle); the signal intensity sensor 6 for detecting the intensity of a signal reflected by a target; a relative distance sensor 7 for sensing a relative distance between the radar device 2D and the target; and the sensitivity difference calculation device 8 for determining a difference in sensitivity between the intensity of signals on the basis of the relative distance from the target detected by the relative distance sensor 7. Information about the azimuth angle $\theta_4$ of the transmission section $a_9$ detected by the relative angle sensor 5 and information about the intensity of the signals transmitted from the transmission sections $a_9$, $a_{10}$, the intensity being detected by the signal intensity sensor 6, are output to the outside by way of the radar 2D. The information is then displayed on a display device (not shown).

Figure 15:
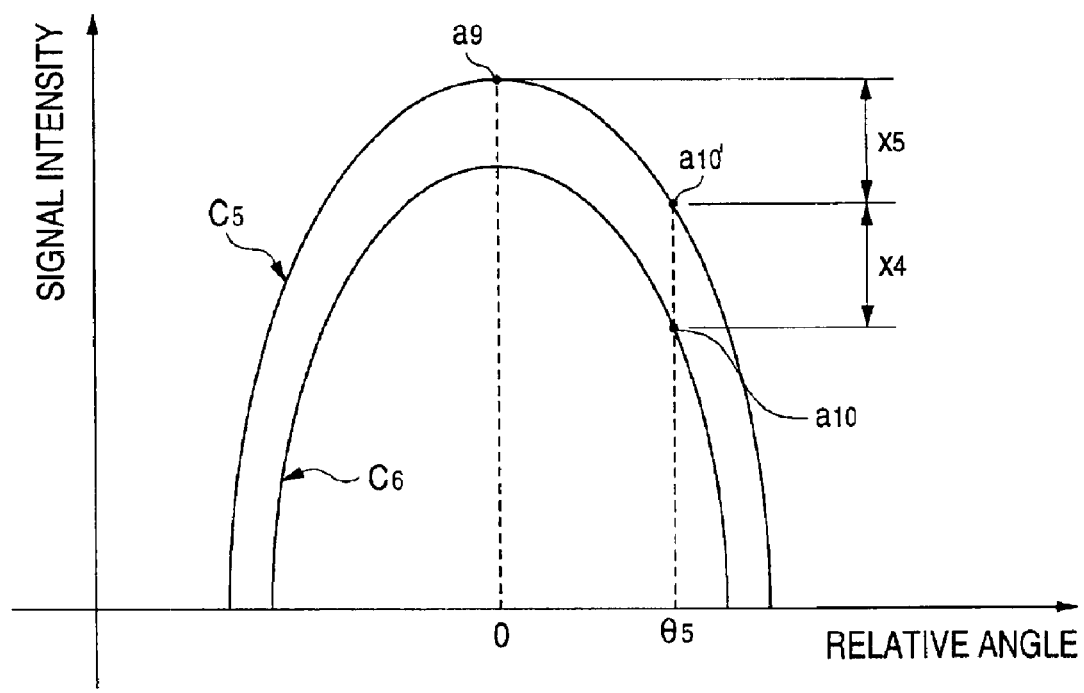
FIG. 15 is a view showing a relationship between the angle of a target with reference to a radar device and reflection intensity.

FIG. 15 shows a relationship between an angle (here an elevation angle) defined between the radar device 2D and the target and the intensity of the signal transmitted from the target. In the drawing, $C_5$ denotes the relationship between the elevation angle of the target (e.g., the transmission section $a_9$) disposed at a position spaced a predetermined distance (several meters) from the radar device 2D and the intensity of the signal transmitted from the target. In the drawing, $C_5$ denotes the relationship between the elevation angle of the target disposed at a position spaced a predetermined distance (several meters) from the radar device 2D and the intensity of the signal transmitted from the target.

As shown in FIG. 15, even when two transmission sections are disposed at different positions relative to the radar device 2D so as assume an identical relative angle with reference to the radar device 2D, the signal transmitted from an object disposed a short distance from the radar device 2D is greater in intensity than that transmitted from an object disposed at a position more distant from the radar device 2D. For instance, the elevation angle of the transmission section $a_{10}$ relative to the radar device 2D and the elevation angle of the transmission section $a_{10}$, relative to the radar device 2D assume identical angles $\theta_5$. However, the signal transmitted from the transmission section $a_{10}$ is greater in intensity than that output from the transmission sections $a_{10}$ by $x_4$.

When the mount direction of the radar device 2D is aligned, the sensitivity difference calculation device 8 computes a sensitivity difference, and the intensity of signals is detected by the signal intensity sensor 6. The transmit/ receive direction of the radar device 2D is aligned such that a difference between the intensity of the signal output from the transmission section $a_9$ and the intensity of the signal output from the transmission section $a_{10}$ that takes into account a sensitivity difference $x_4$ assumes a predetermined intensity difference level (here $x_5$). Moreover, the transmit/receive direction of the radar device 2D is aligned such that the azimuth angle $\theta_4$ becomes a predetermined angle (e.g., 0 degree) while the azimuth angle $\theta_4$ is detected by the relative angle sensor 5.

If the transmit/receive direction of the radar device 2D is aligned such that the intensity difference assumes a predetermined intensity difference level $x_5$, the transmit/receive direction of the radar device 2D is aligned such that the elevation angle of the transmission section $a_9$ relative to the radar device 2D becomes 0 degree. In contrast, if the transmit/receive direction of the radar device 2D is aligned such that the azimuth angle $\theta_4$ assumes 0 degree, a center $L_7$ of the radar device 2D is aligned with the center line Lc.

Under the method of aligning a radar mount direction according to the seventh embodiment, the transmit/receive direction of the radar device 2D is aligned in the azimuth plane on the basis of the relative angle detected by the relative angle sensor 5. Further, the transmit/receive direction of the radar device 2D is aligned in the elevation plane on the basis of the intensity of the signal detected by the signal intensity sensor 6. As a result, the mount direction of the radar device 2D can be accurately aligned with respect to both azimuth and elevation.

Although the method of aligning a radar according to the seventh embodiment has adopted the radar mount direction alignment devices $D_1$, $D_2$ such as those shown in FIG. 2A, a method of aligning a radar mount direction according to another embodiment may adopt radar mount direction alignment devices such as those shown in FIGS. 2B, 3A, and 3B.

Eighth Embodiment

Figure 16A:
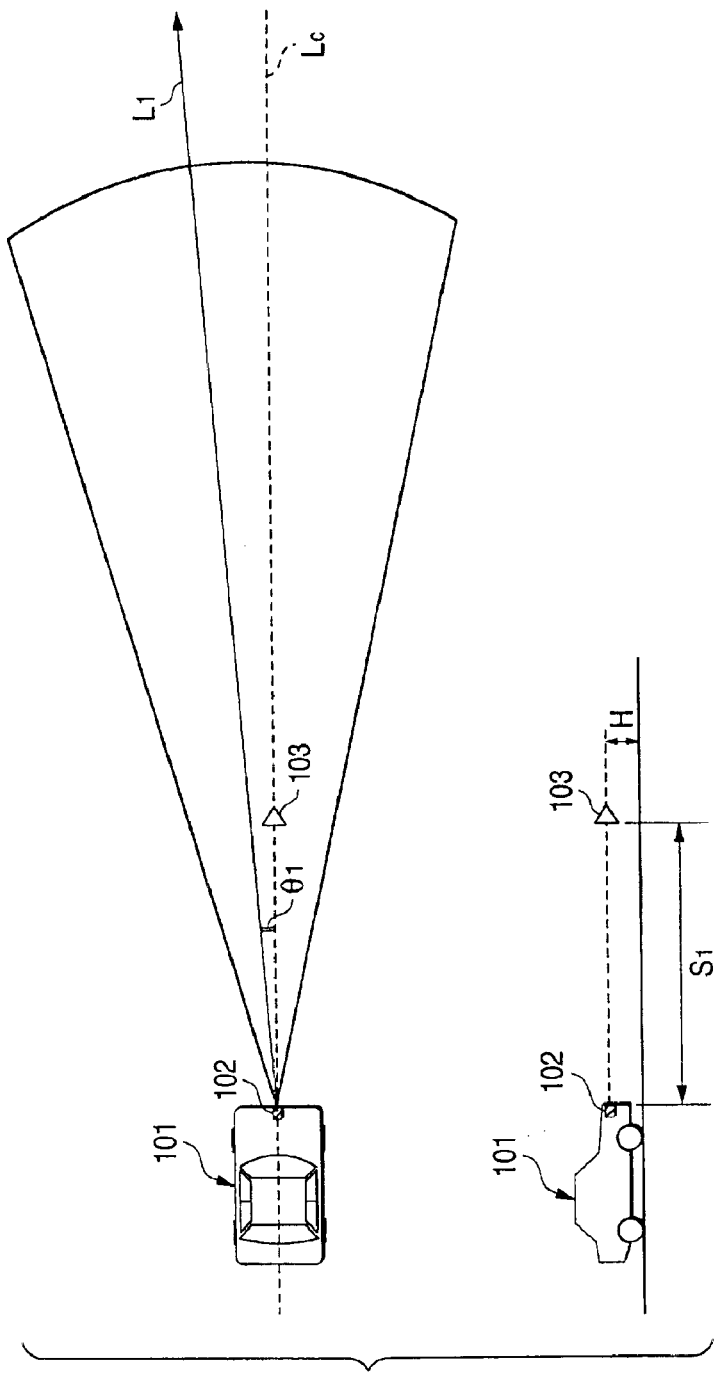
FIG. 16A is a descriptive view for describing a method of aligning a radar mount direction according to an eighth embodiment of the present invention.

A method of aligning a radar mount direction according to an eighth embodiment of the present invention will now be described, by means of taking as an example a case where a transmit/receive direction of a radar device 102 mounted on a vehicle 101 is to be aligned. As shown in FIG. 16A, a reflection target 103 is disposed at a position (i.e., the position of a target with which the mount direction of the radar device 102 is to be aligned) spaced distance $S_1$ (e.g., 10 meters) from the vehicle 110. The radar device 102 and the reflection target 103 are placed at a height "h" and at positions along a longitudinal center line Lc of the vehicle 101. Further, $\theta_1$ provided in the drawing denotes the angle of the reflection target 103 with reference to the center line $L_1$ of the sensing area of the radar device 102.

Figure 16B:
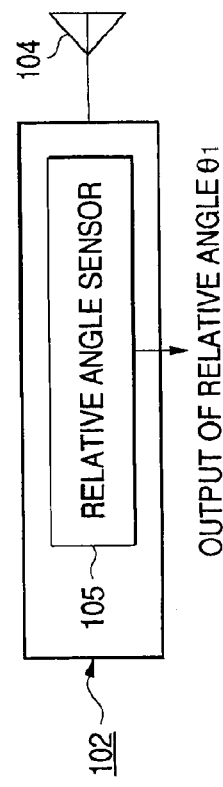
FIG. 16B is a block diagram schematically showing the principal section of a radar device.

As shown in FIG. 16B, the radar device 102 is equipped with a transmit/receive antenna 104 which rotates within a horizontal plane, and a relative angle sensor 105 for sensing a relative angle (an azimuth angle in this case) with reference to the target. Information about the angle $\theta_1$ of the reflection target 103 detected by the relative angle sensor 105 is output to the outside from the radar device 102. The information is then displayed on a display device (not shown).

When the mount direction of the radar device 102 is aligned, the transmit/receive direction of the radar device 102 is aligned such that the angle $\theta_1$ assumes a predetermined value (e.g., 0 degree) while the angle $\theta_1$ is detected by the relative angle sensor 105.

Under the method for aligning a radar mount direction according to the eighth embodiment, the reflection target 103 is provided on the longitudinal center line Lc of the vehicle 101 and at the position spaced $S_1$ from the vehicle 101. The transmit/receive direction of the radar device 102 is aligned such that the angle $\theta_1$ of the reflection target 103 with reference to the radar device 102 detected by the relative angle sensor 105 assumes a predetermined angle. Thus, the mount direction of the radar device 102 can be aligned accurately.

Ninth Embodiment

A method of aligning a radar mount direction according to a ninth embodiment of the present invention will now be described. As shown in FIG. 17A, the radar device 102 is mounted on the front right section of the vehicle 101. Position T is set on the longitudinal center line Lc of the vehicle 101 and at a location (i.e., the position of a target with which the mount direction of the radar device 102 is to be aligned) spaced a distance $S_2$ (e.g., 100 meters) from the vehicle 101. The reflection target 103 is disposed on a line $L_T$ connecting the radar device 102 with the position T. Here, the radar device 102 and the reflection target 103 are placed at a height "h". Further, the reflection target 103 is provided at a position spaced from the vehicle 101 by distance $S_3$ (e.g., 10 meters) In the drawing, $\theta_2$ denotes the angle of the reflection target 103 with reference to the center line $L_2$ of the radar device 102.

As shown in FIG. 17B, the radar device 102 is equipped with a transmit/receive antenna 104 which rotates within a horizontal plane, and a relative angle sensor 105 for sensing a relative angle (an azimuth angle in this case) with reference to the target. Information about the angle $\theta_2$ of the reflection target 103 detected by the relative angle sensor 105 is output to the outside from the radar device 102. The information is then displayed on a display device (not shown).

When the mount direction of the radar device 102 is aligned, the transmit/receive direction of the radar device 102 is aligned such that the angle $\theta_2$ assumes a predetermined value (e.g., 0 degree) while the angle $\theta_2$ is detected by the relative angle sensor 105.

Under the method of aligning a radar mount direction according to the ninth embodiment, the reflection target 103 is disposed on the line $L_T$ that connects the mount position of the radar device 102 with the position T serving as the position of a target with which the mount direction of the radar device 102 is to be aligned. The transmit/receive direction of the radar device 102 is aligned such that the angle $\theta_2$ of the reflection target 103 with reference to the radar device 102 detected by the relative angle sensor 105 assumes a predetermined angle. Thus, the mount direction of the radar device 102 can be aligned accurately.

As shown in FIG. 17A, the transmit/receive direction of the radar device 102 can be aligned such that the vehicle driving ahead at the position T (e.g., a vehicle driving ahead of the vehicle 101 at a distance of 100 meters) can be captured without fail unless the reflection target 103 is provided at the position T that serves as the position of a target with which the mount direction of the radar device 102 is to be aligned.

Hence, even when the transmit/receive direction of the radar device 102 is aligned in a limited space in which the position T serving as a target for alignment cannot be ensured, the transmit/receive direction of the radar device 102 can be aligned such that a target (e.g., a vehicle driving ahead) located at the position T that serves as a target for alignment can be captured without fail, by adoption of the radar mount direction alignment method.

Tenth Embodiment

Figure 18A:
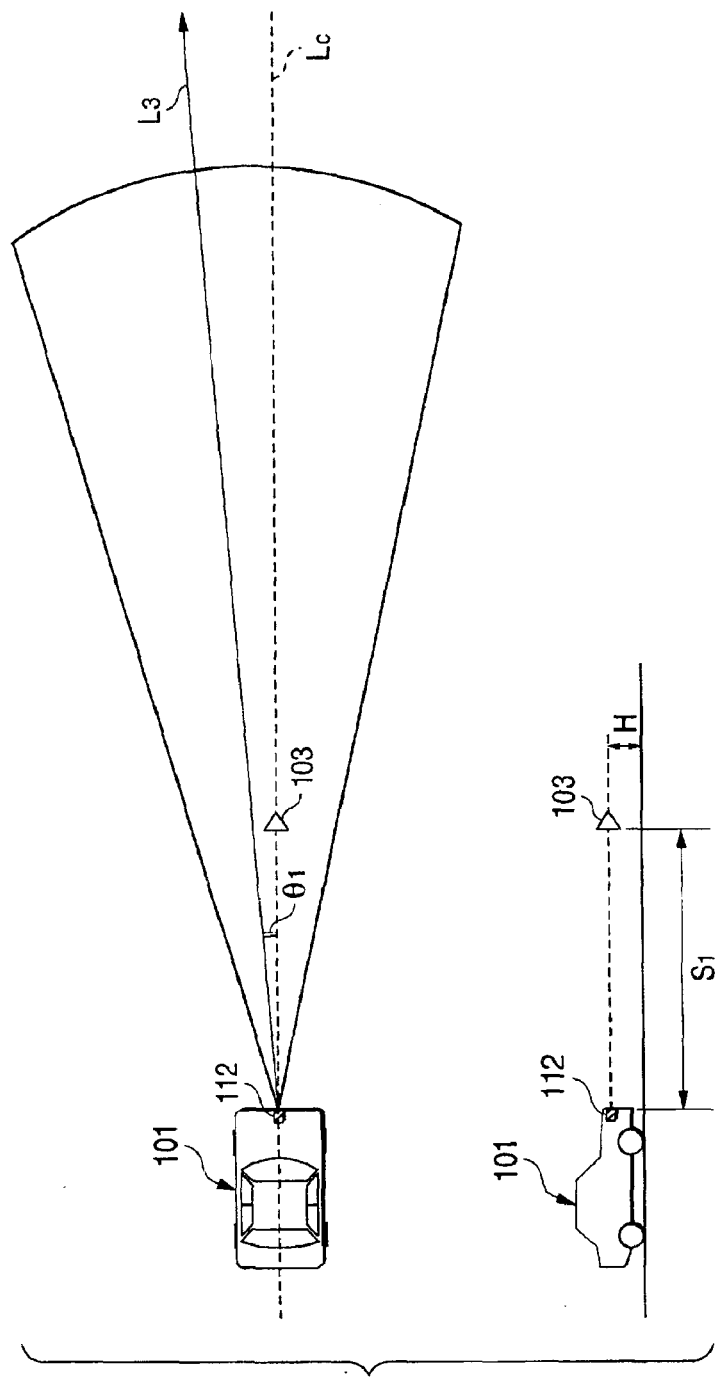
FIG. 18A is a descriptive view for describing a method of aligning a radar mount direction according to a tenth embodiment of the present invention.

A method of aligning a radar mount direction according to a tenth embodiment of the present invention will now be described. As shown in FIG. 18A, a radar device 112 is provided on the front of the vehicle 101. The reflection target 103 is disposed at a position spaced distance $S_1$ (e.g., 10 meters) from the vehicle 101. The radar device 112 and reflection target 103 are placed at a height "h" and in positions along a longitudinal center line Lc of the vehicle 101. Further, $\theta_1$ provided in the drawing denotes the angle of the reflection target 103 with reference to the center line $L_3$ of sensing area of the radar device 112.

Figure 18B:
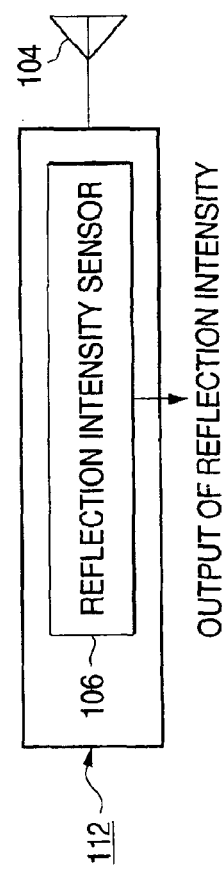
FIG. 18B is a block diagram schematically showing the principal section of a radar device.
Figure 19:
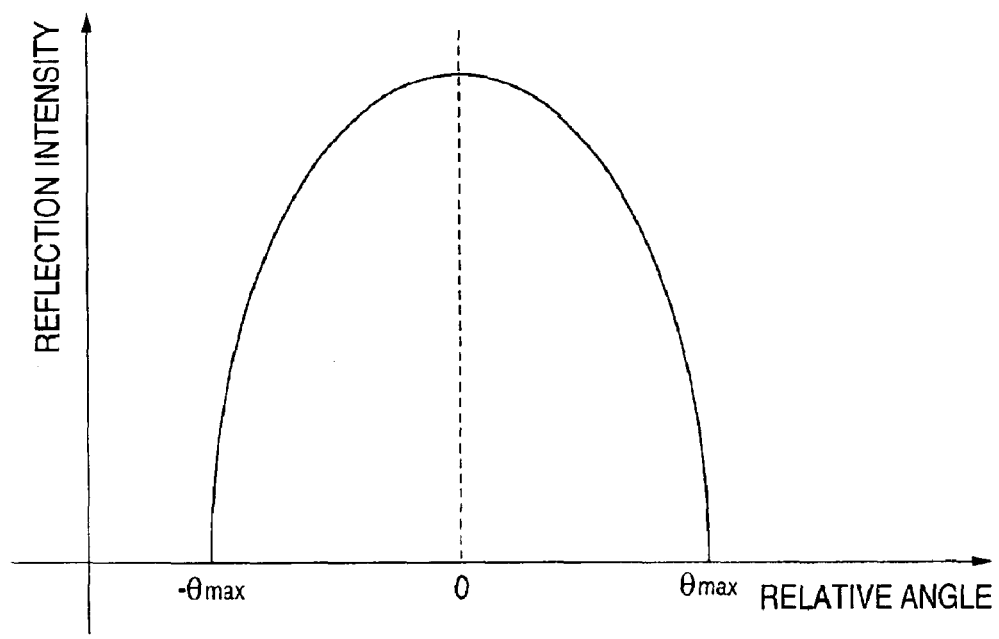
FIG. 19 is a view showing a relationship between the angle of a target with reference to a radar device and reflection intensity.

As shown in FIG. 18B, the radar device 112 is equipped with a transmit/receive antenna 104, and a reflection intensity sensor 106 for detecting the intensity of a signal reflected by a target. Information about the intensity of the signal reflected by the reflection target 103 detected by the reflection intensity sensor 106 is output to the outside from the radar device 112. The information is then displayed on a display device (not shown). As shown in FIG. 19, the intensity of the signal reflected by the reflection target 103 becomes maximum when the angle $\theta_1$ of the reflection target 103 relative to the radar device 112 assumes 0 degree. As the value of the reflection angle $\theta_1$ becomes greater, the intensity of the reflected signal becomes smaller.

When the mount direction of the radar device 112 is aligned, the transmit/receive direction of the radar device 112 is aligned such that the intensity of a reflected signal assumes a predetermined level (e.g., a maximum level) while the intensity of a reflected signal is detected by the reflection intensity sensor 106.

Under the method of aligning a radar mount direction according to the tenth embodiment, the reflection target 103 is provided on the longitudinal center line Lc of the vehicle 101 and at the position spaced $S_1$ from the vehicle 101. The transmit/receive direction of the radar device 102 is aligned such that the intensity of the signal reflected by the reflection target 103 and detected by the reflection intensity sensor 106 assumes a predetermined level. Thus, the mount direction of the radar device 112 can be aligned accurately.

Eleventh Embodiment

Figure 20A:
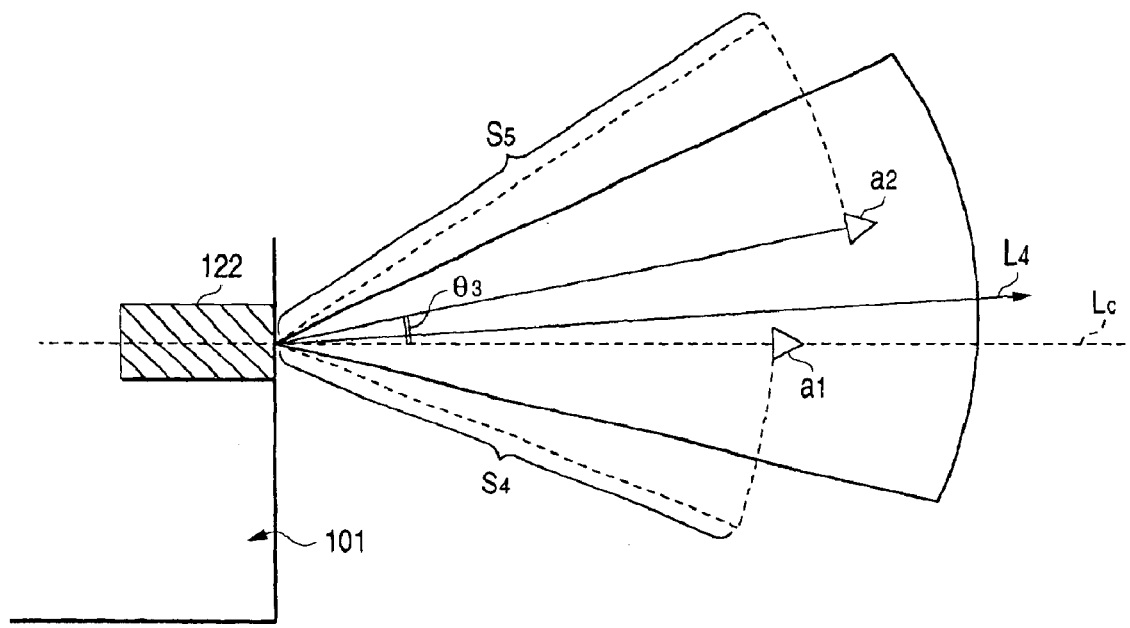
FIG. 20A is a descriptive view for describing a method of aligning a radar mount direction according to an eleventh embodiment of the present invention.

A method of aligning a radar mount direction according to an eleventh embodiment of the present invention will now be described. As shown in FIG. 20A, a radar device 122 is mounted on the front of the vehicle 101. A reflection target $a_1$ is disposed at a position spaced distance $S_4$ (e.g., 10 meters) from the vehicle 101. Further, another reflection target $a_2$ is disposed at a position spaced distance $S_5$ (e.g., 15 meters) from the vehicle 101. The reflection target $a_1$ is provided on the longitudinal center line Lc of the vehicle 101, and the reflection target $a_2$ is provided at a position offset from the center line Lc by angle $\theta_3$.

Figure 20B:
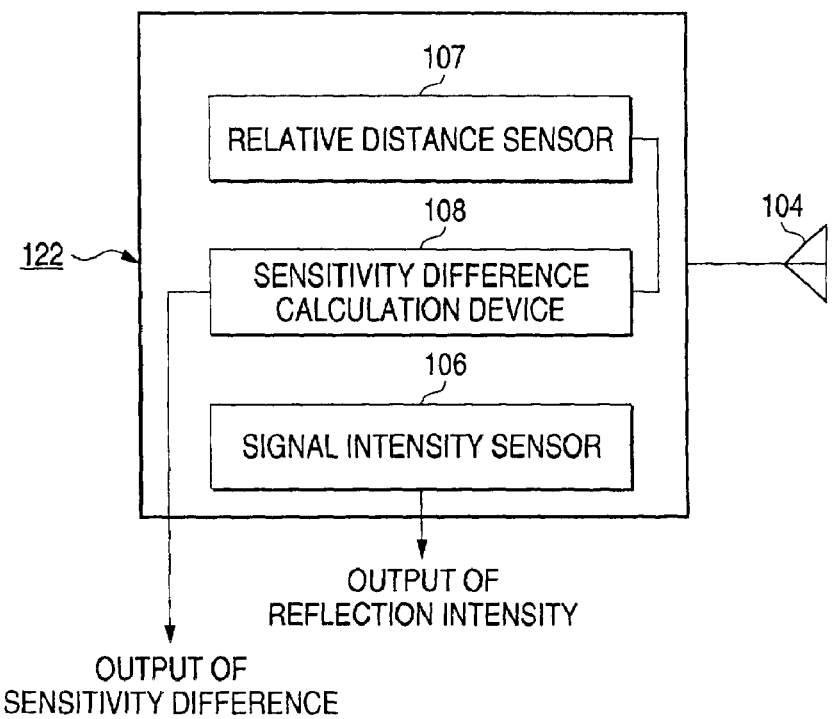
FIG. 20B is a block diagram schematically showing the principal section of a radar device.

As shown in FIG. 20B, the radar device 122 is equipped with the transmit/receive antenna 104; the reflection intensity sensor 106 for detecting the intensity of a signal reflected by a target; a relative distance sensor 107 for sensing a relative distance between the radar device 122 and the target; and a sensitivity difference calculation device 108 for determining a difference in sensitivity between the intensity of signals on the basis of the relative distance from the target detected by the relative distance sensor 107. Information about the intensity of signals reflected by the reflection targets $a_1$, $a_2$ detected by the reflection intensity sensor 106 and information about sensitivity difference are output to the outside of the radar device 122. The information is then displayed on a display device (not shown).

Methods of determining a sensitivity difference include a method of determining a sensitivity difference using a radar equation, and a method of determining a sensitivity difference using the information stored in the memory which stores information about a sensitivity difference appropriate to a relative distance from the target.

Figure 21:
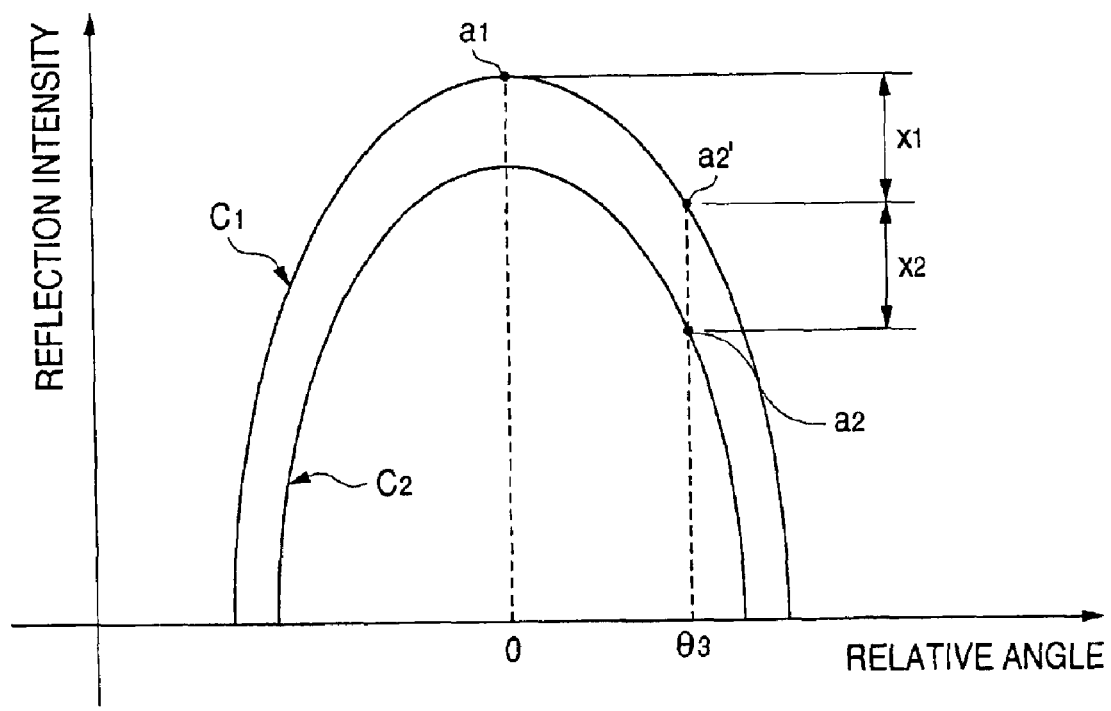
FIG. 21 is a view showing a relationship between the angle of a target with reference to a radar device and reflection intensity.

FIG. 21 shows a relationship between an angle defined between the radar device 122 and the reflection target and the intensity of the signal transmitted from the reflection target. In the drawing, $C_1$ denotes the relationship between the angle of the reflection target $a_1$ disposed at a position spaced from the radar device 122 by distance $S_4$ and the intensity of the signal reflected by the reflection target $a_1$. In the drawing, $C_2$ denotes the relationship between the angle of the reflection target $a_2$ disposed at a position spaced from the radar device 122 by distance $S_5$ and the intensity of the signal transmitted from the reflection target $a_2$.

As shown in FIG. 21, even when two reflection targets are disposed at different positions relative to the radar device 122 so as assume identical relative angles with reference to the radar device 122, the signal transmitted from the target $a_1$ disposed a short distance from the radar device 122 is greater in intensity than that transmitted from the target $a_2$ disposed at a position more distant from the radar device 122. For instance, the angle defined between the radar device 122 and the reflection target $a_2$ and the angle defined between the radar device 122 and a reflection target $a_2$, assume identical angles $\theta_3$. However, the signal output from the reflection target $a_2$, is greater in intensity than that output from the reflection target $a_2$ by $x_2$.

When the mount direction of the radar device 122 is aligned, the sensitivity difference calculation device 108 computes a sensitivity difference, and the intensity of reflected signals is detected by the reflection intensity sensor 106. The transmit/receive direction of the radar device 122 is aligned such that a difference between the intensity of the signal reflected by the reflection target $a_1$ and the intensity of the signal output from the reflection target $a_2$ that takes into account a sensitivity difference $x_2$ assumes a predetermined level ($x_1$ in this case).

For instance, if the transmit/receive direction of the radar device 122 is aligned such that the intensity difference assumes a predetermined level $x_1$, the transmit/receive direction of the radar device 122 is aligned such that the angle of the reflection target $a_1$ relative to the radar device 122 assumes 0 degree, as shown in FIG. 21.

Under the method of aligning a radar mount direction according to the eleventh embodiment, a difference in sensitivity between the intensity of signals which are susceptible to the influence of distance is taken into consideration. Hence, the reflection targets $a_1$, $a_2$ are disposed, and the transmit/receive direction of the radar device 122 can be aligned accurately through use of the intensity of the signals reflected by the reflection targets $a_1$, $a_2$.

Twelfth Embodiment

Figure 22A:
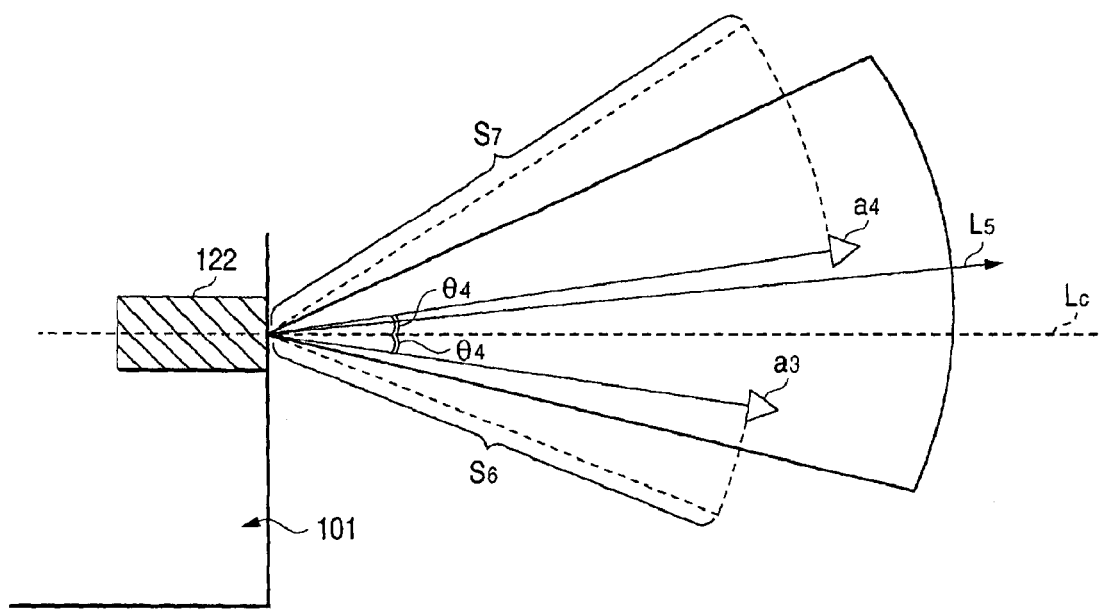
FIG. 22A is a descriptive view for describing a method of aligning a radar mount direction according to a twelfth embodiment of the present invention.

A method of mounting a radar mount direction according to a twelfth embodiment of the present invention will now be described. As shown in FIG. 22A, the radar device 122 is mounted on the front of the vehicle 101. A reflection target a3 is disposed at a position spaced distance $S_6$ (e.g., 10 meters) from the vehicle 101. Further, another reflection target $a_4$ is disposed at a position spaced distance $S_6$ (e.g., 15 meters) from the vehicle 101. The reflection targets $a_3$, $a_4$ are provided in opposite directions from the longitudinal center line Lc of the vehicle 1, by angle $\theta_4$ from the longitudinal center line.

Figure 22B:
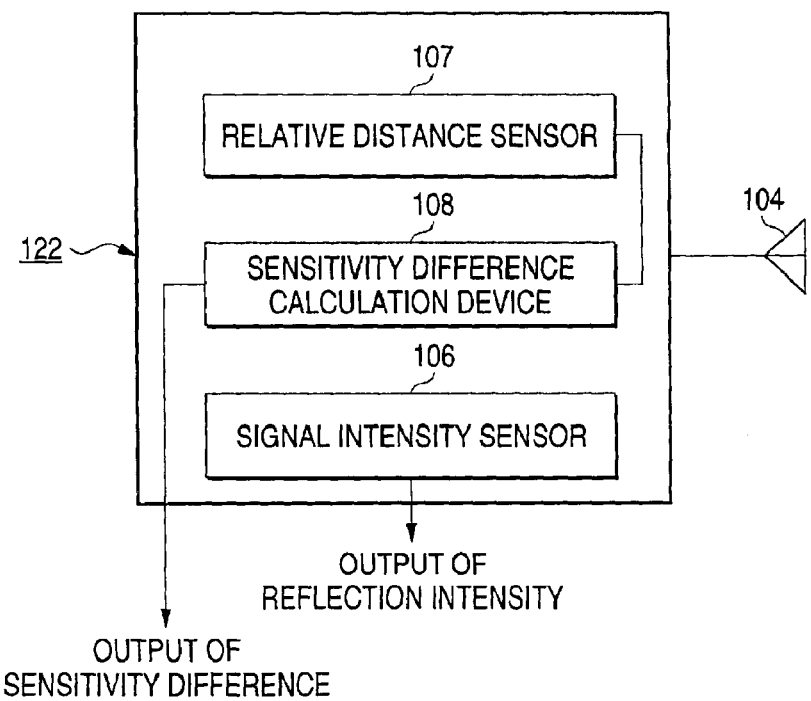
FIG. 22B is a block diagram schematically showing the principal section of a radar device.

As shown in FIG. 22B, the radar device 122 is equipped with the transmit/receive antenna 104; the reflection intensity sensor 106 for detecting the intensity of a signal reflected by a target; the relative distance sensor 107 for sensing a relative distance between the radar device 122 and the target; and the sensitivity difference calculation device 108 for determining a difference in sensitivity between the intensity of signals which are susceptible to the influence of distance, on the basis of the relative distance from the target detected by the relative distance sensor 107. Information about the intensity of signals reflected by the reflection targets $a_3$, $a_4$ detected by the reflection intensity sensor 106 and information about sensitivity difference are output to the outside of the radar device 122. The information is then displayed on a display device (not shown).

Figure 23:
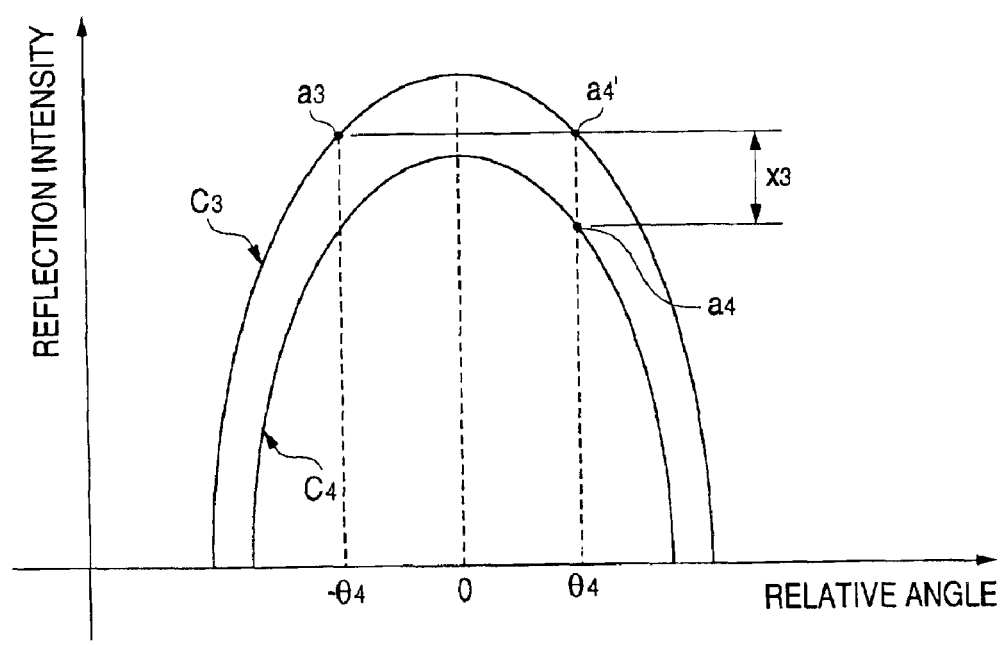
FIG. 23 is a view showing a relationship between the angle of a target with reference to a radar device and reflection intensity.
Figures 24A, 24B, 24C, 24D:
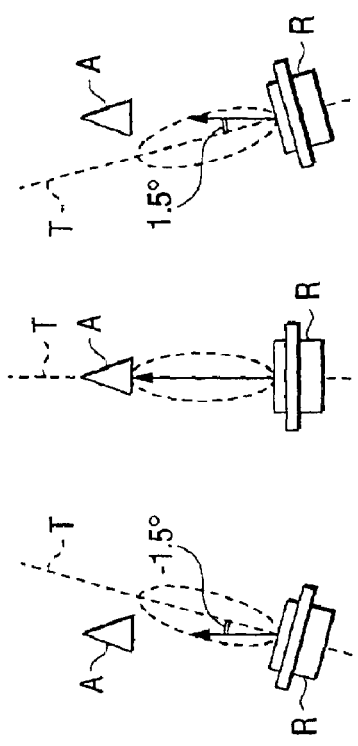
FIG. 24A is a view showing an example relationship between a beam direction of the radar device and a directional pattern.
FIGS. 24B through 24D are views for describing a positional relationship between the radar device and an antenna.
Figure 25A:
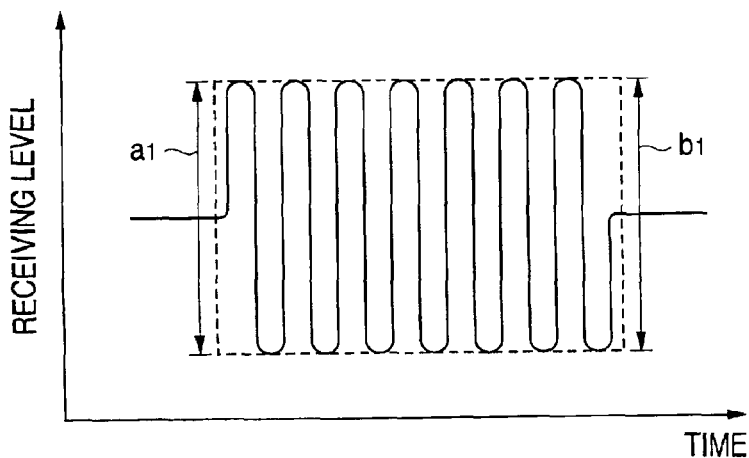
FIGS. 25A through 25C are each views showing an example of a change in the level of a signal received by a receiving section in accordance with a positional relationship between a radar device and the receiving section.
Figure 25B:
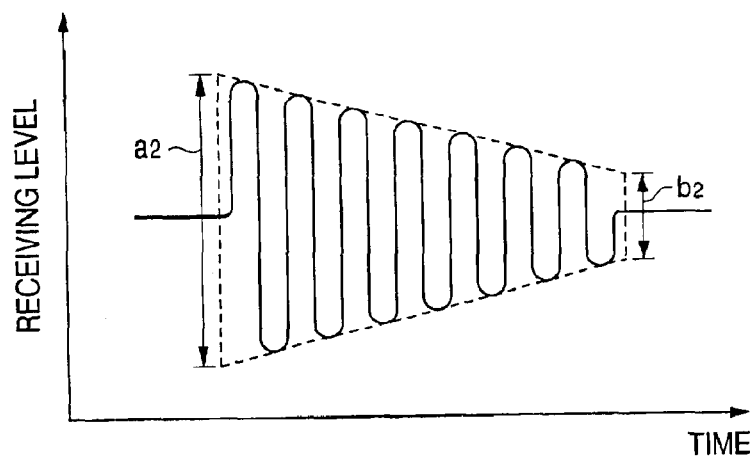
Figure 25C:
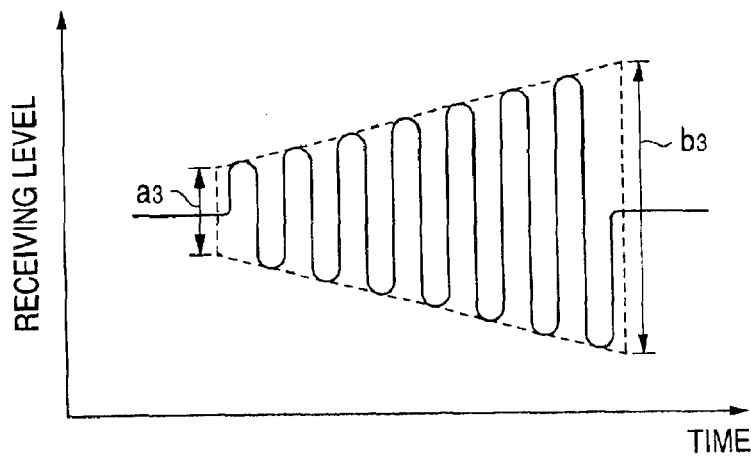

FIG. 23 shows a relationship between an angle defined between the radar device 122 and the reflection target and the intensity of the signal transmitted from the reflection target. In the drawing, $C_1$ denotes the relationship between the angle of the reflection target $a_3$ disposed at a position spaced distance $S_6$ from the radar device 122 and the intensity of the signal reflected by the reflection target $a_3$. In the drawing, $C_4$ denotes the relationship between the angle of the reflection target $a_4$ disposed at a position spaced distance $S_7$ from the radar device 122 and the intensity of the signal transmitted from the reflection target $a_4$. As shown in FIG. 23, even when two reflection targets are disposed at different positions relative to the radar device 122 so as assume identical relative angles with reference to the radar device 122, the signal transmitted from the target $a_3$ disposed a short distance from the radar device 122 is greater in intensity than that transmitted from the target $a_4$ disposed at a position more distant from the radar device 122. For instance, the angle defined between the radar device 122 and the reflection target $a_3$ and the angle defined between the radar device 122 and reflection targets $a_4$, $a_4$, assume identical angles $\theta_4$. However, the signals output from the reflection targets $a_3$, $a_4$, are greater in intensity than that output from the reflection target $a_4$, by $x_3$.

When the mount direction of the radar device 122 is aligned, the sensitivity difference calculation device 108 computes a sensitivity difference, and the intensity of reflected signals is detected by the reflection intensity sensor 106. The transmit/receive direction of the radar device 122 is aligned so as to eliminate a difference between the intensity of the signal reflected by the reflection target $a_3$ and the intensity of the signal output from the reflection target $a_4$ that takes into account a sensitivity difference $x_3$.

If the transmit/receive direction of the radar device 122 is aligned such that the intensity difference is eliminated, the transmit/receive direction of the radar device 122 is aligned such that the angles defined between the reflection target $a_3$, $a_4$ relative to the radar device 122 assume $\theta_4$, as shown in FIG. 23. More specifically, the center line $L_5$ of the sensing area of the radar device 122 is aligned exactly with the center line Lc.

Under the method of aligning a radar mount direction according to the twelfth embodiment, a difference insensitivity between the intensity of signals which are susceptible to the influence of distance is taken into consideration. Hence, the reflection targets $a_3$, $a_4$ are disposed, and the transmit/receive direction of the radar device 122 can be aligned accurately through use of the intensity of the signals reflected by the reflection targets $a_3$, $a_4$.

The methods for aligning a radar mount direction described in connection with the eighth through twelfth embodiments have described only a case where the mount directions of the radar devices 102, 112, and 122 are aligned within a horizontal plane. However, the mount direction of a radar device can be aligned in the same manner even when the radar devices 102, 112, and 122 are equipped with a transmit/receive antenna which is pivotable in a vertical plane and when the mount directions of the radar devices 102, 112, and 122 are aligned in a vertical plane.

If reflection targets are disposed such that any one of the methods described in connection with the eighth through twelfth embodiments is taken as a method of aligning a mount direction in a horizontal plane and such that another one of the methods is taken as a method of aligning a mount direction in a vertical plane, biaxial alignment of a mount direction can be effected simultaneously and efficiently.

Thirteenth Embodiment

Another embodiment of the method of aligning a radar mount direction according to the present invention and another embodiment of the device for aligning a radar mount direction according to the present invention will now be described by reference to the accompanying drawings.

Figure 26:
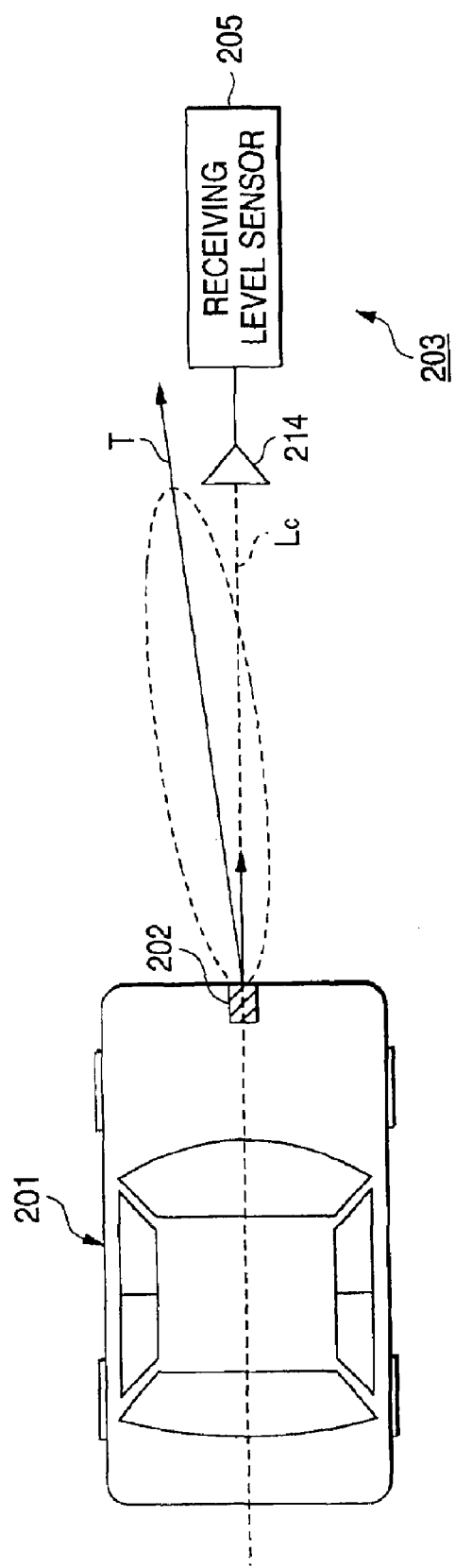
FIG. 26 is a descriptive view for describing a method of aligning a radar mount direction according to a thirteenth embodiment of the present invention.

A thirteenth embodiment of the present invention will now be described, by means of taking as an example a case where the transmit/receive direction of a radar device 202 mounted on a vehicle 201 is to be aligned. As shown in FIG. 26, a radar device 202 having a beam scanning function is mounted on the front of the vehicle 201. An antenna 204 constituting a radar mount direction alignment device 203 is disposed at a position spaced distance $S_1$ from the vehicle 201 (i.e., at the position of a target with which the mount direction of the radar device 202 is to be aligned). A mechanical beam scan antenna or a phased array antenna can be used as a beam scan antenna to be provided in the radar device 202.

The radar mount direction alignment device 203 is equipped with a receiving level sensor 205 for sensing the receiving level of a signal received by the antenna 204. Information about the receiving level detected by the receiving level sensor 205 is output to the outside, and the information is then displayed on a display device (not shown).

Figure 27:
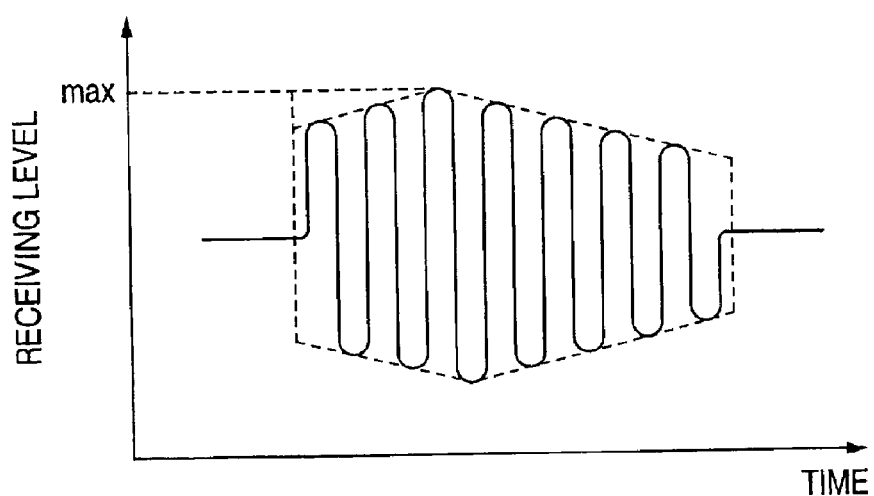
FIG. 27 is a view showing one example of changes in the level of a signal received by an antenna.

The radar device 202 and the antenna 204 are provided at identical heights and on the longitudinal center line Lc of the vehicle 201. In the drawing, T denotes the center direction of beam scanning range of the radar device 202 (i.e., the center axis and front directions of the radar device) When the mount direction of the radar device 202 is aligned, a signal is emitted in the vicinity of the center axis of the radar device. In accordance with changes in the level of the signal received by the antenna 204, the transmit/receive direction of the radar device 202 is aligned. FIG. 27 shows an example of changes in the level of the signal received by the antenna 204.

In connection with an example of changes in level shown in FIG. 27, the maximum level of the received signal lies not in the center position on the time axis but in the range of level changes. Hence, the longitudinal center line Lc of the vehicle 201 can be aligned with the center direction T of beam scanning range of the radar device 202, by means of aligning the transmit/receive direction of the radar device 202 such that the maximum level of the received signal appears in the center position of the range of level change.

The method of aligning the transmit/receive direction of the radar device 202 in accordance with changes in the level of the received signal includes the following methods "a" through "c."

a: In relation to level changes, the current status of the radar device 202; that is, a mounted state of the radar device 202, is ascertained, and the transmit/receive direction of the radar device 202 is aligned, by use of a balance in level change or a difference between a level at one end of a scanning range and a level at the other end of the scanning range with reference to the scan direction.

b: In relation to level changes, information about the ends of a scanning range with reference to a scan direction; that is, the level of a signal received by the antenna 204 immediately after emission of a signal from the radar device 202 has been commenced and/or the level of a signal received by the antenna 204 immediately before emission of a signal from the radar device 202 is ceased, is not used for alignment.

c: Amplitude information (e.g., the maximum peak value and the minimum peak value) which becomes an explicit standard is used.

Under the method of aligning a radar mount direction according to the thirteenth embodiment, the antenna 204 constituting a radar mount direction alignment device 203 is disposed at the position spaced distance $S_1$ from the vehicle 201 and on the longitudinal center line Lc of the vehicle 201. The transmit/receive direction of the radar device 202 is aligned in accordance with a change in the level of the signal that has been emitted from the radar device 202 and received by the antenna 204 such that a change in the level attains a desired value. As a result, the mount direction of the radar device can be aligned accurately.

Figure 28:
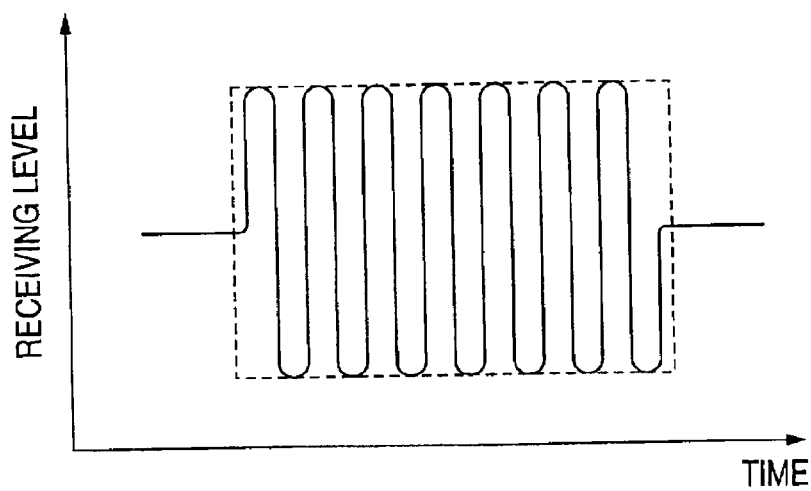
FIG. 28 is a view showing one example of changes in the level of a signal received by an antenna.
Figure 29:
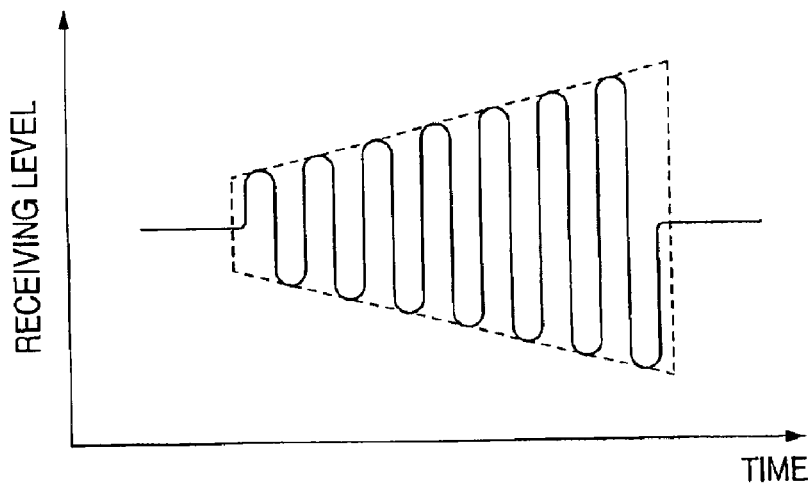
FIG. 29 is a view showing one example of changes in the level of a signal received by an antenna.

FIGS. 28 and 29 show examples of changes in the level of a received signal. The transmit/receive direction of the radar device 202 is aligned so as to attain a change in level which has superior balance between the right scan direction and the left scan direction, whereby the longitudinal center line Lc of the vehicle 201 can be aligned with the main beam direction T of the radar device 202.

The center direction T of beam scanning range of the radar device 202 can be oriented toward a desired direction, by means of aligning the transmit/receive direction of the radar device 202 such that a desired level difference is realized between the level of the right scan direction and the level of the left scan direction. From the level difference, the angle of the antenna 203 relative to the center direction T of beam scanning range of the radar device 202 can be determined. In other words, a desired level difference can be determined from a desired relative angle.

Fourteenth Embodiment

Figure 30:
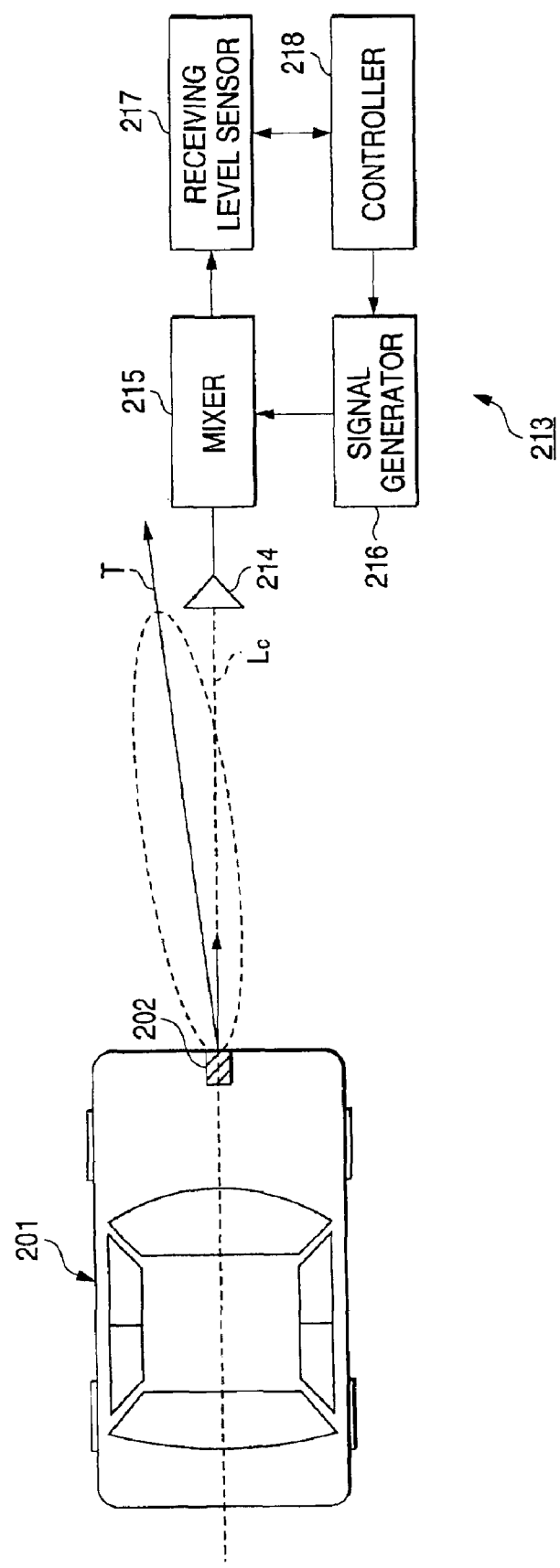
FIG. 30 is a descriptive view for describing a method of aligning a radar mount direction according to a fourteenth embodiment of the present invention.

A method of aligning a radar mount direction according to a fourteenth embodiment of the present invention will now be described. As shown in FIG. 30, the radar device 202 having a beam scanning function is mounted on the front of the vehicle 201. An antenna 214 constituting a radar mount direction alignment device 213 is disposed at a position spaced distance $S_1$ from the vehicle 201 (i.e., at the position of a target with which the mount direction of the radar device 202 is to be aligned).

The radar mount direction alignment device 213 comprises the antenna 214; a mixer circuit 215 which acts as a frequency converter for converting a frequency $f_0$ of the signal received by the antenna 214 into an intermediate frequency IF; a signal generator 216 for outputting a signal of frequency $f_a$ (=IF−$f_0$) to the mixer circuit 215; a receiving level sensor 217 which acquires an intermediate frequency IF signal converted by the mixer circuit 215 and detects a receiving level; and a controller 218 which performs a control operation so as to acquire information about the frequency of a signal detected by the receiving level sensor 217 and to cause the signal generator 216 to output a signal of predetermined frequency to the mixer circuit 215. Information about the receiving level detected by the receiving level sensor 217 is output to the outside, and the information is then displayed on a display device (not shown).

The radar device 202 and the antenna 214 are provided at identical heights and at positions along the longitudinal center line Lc of the vehicle 201. In the drawing, T denotes the center direction of the beam scanning range of the radar device 202.

When the mount direction of the radar device 202 is aligned, a signal (CW signal) is emitted toward the center direction of the beam scanning range. In accordance with a change in the level of the signal received by the antenna 214, the transmit/receive direction of the radar device 202 is aligned.

Under the method of aligning a radar mount direction according to the fourteenth embodiment, the antenna 214 constituting the radar mount direction alignment device 213 is disposed at the position spaced distance $S_1$ from the vehicle 201. The transmit/receive direction of the radar device 202 is aligned in accordance with a change in the level of the signal that has been emitted from the radar device 202 and received by the antenna 214, so as to attain a desired level change. Thus, the mount direction of the radar device can be aligned accurately.

The receiving level sensed by the receiving level sensor 217 is an intermediate frequency signal. Hence, changes in the level of a received signal can be readily displayed on an electronic device such as an oscilloscope.

The method of aligning a radar mount direction according to the thirteenth (or fourteenth) embodiment has been described by reference to only a case where the transmit/receive direction of the radar device 202 is aligned in accordance with changes in the level of the signal received by the antenna 204 or 214 disposed at only one position. Under a method of aligning a radar mount direction according to another embodiment, the antennas 204 and 214 and other antennas may be disposed at different positions. The transmit/receive direction of the radar device 202 may be aligned in accordance with changes in the level of the signal received by at least two or more antennas 204, 214. In this case, alignment can be made more certain.

For instance, even when a failure has arisen in the radar device 202 and no beam scanning is possible, performance of erroneous alignment can be prevented, and occurrence of failure can also be determined.

The system of the present invention has described a method of aligning the mount direction of a radar device, by means of receiving a wave transmitted from the radar device through beam scanning. However, a wave can be transmitted toward a radar device from a radar mount direction alignment device. By reference to information about the level of the wave received by the radar device in the vicinity of the center of a receiving beam scanning range, the mount direction of the radar device can also be aligned.

Fifteenth Embodiment

Figure 31:
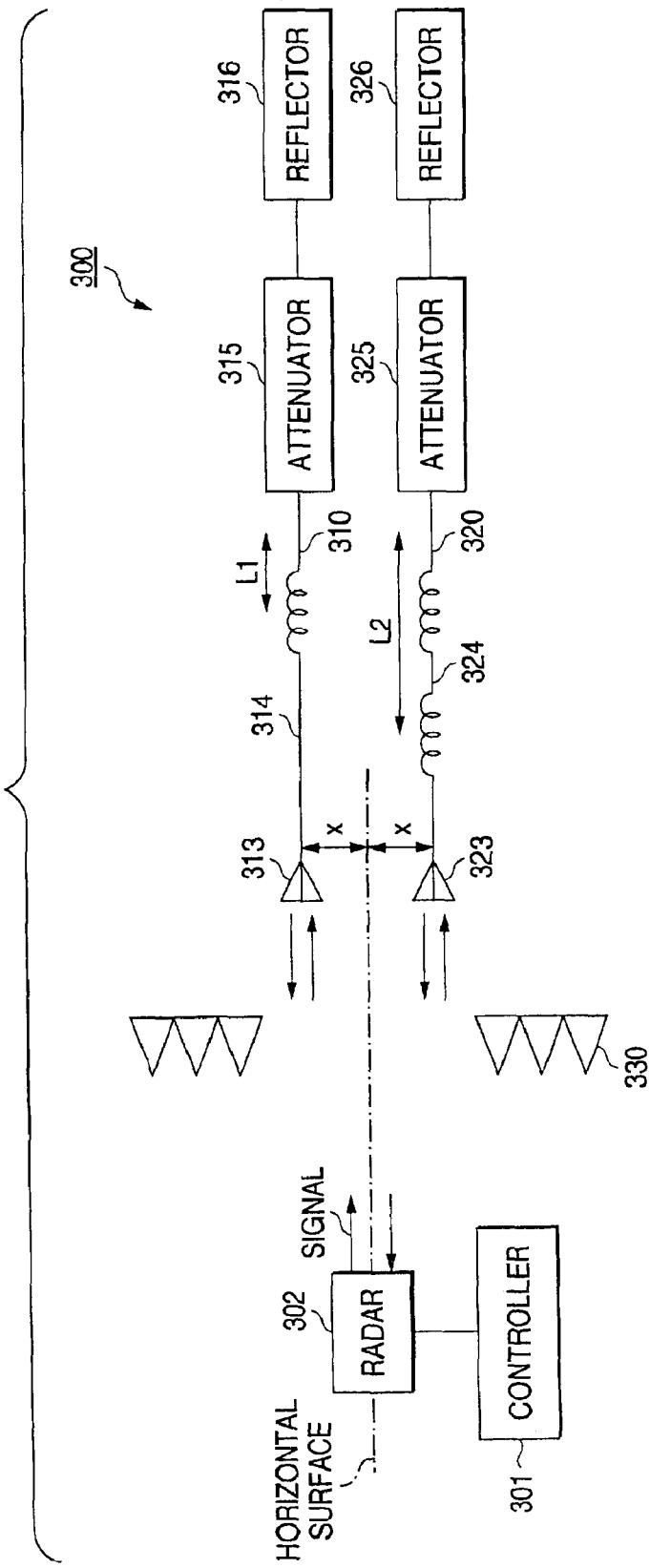
FIG. 31 shows a side view showing a radar mount direction alignment system according to a fifteenth embodiment of the present invention.

FIG. 31 shows a side view showing a radar mount direction alignment system 300 according to a fifteenth embodiment of the present invention.

The radar mount direction alignment system 300 includes a radar 302, a controller 301 for controlling the radar 302, and two reflection units 310 and 320 each disposed in front of the radar 302. Radar wave absorbers 330 are disposed above and below a line connecting the radar 302 and the reflection units 310 and 320.

The radar 302, as well as the radar device 2 in FIG. 1A, is mounted on a front center of a vehicle. The radar 302 transmits a predetermined signal to scan in the horizontal direction of the vehicle. The radar 302 scans so that the signal propagates in the vehicle traveling direction parallel to the horizontal direction. The signal reflects on a reflector existing in the scanning direction, and is received by the radar 302.

The controller 301 analyzes the signal received by the radar 302, and determines misalignment of the radar mount direction based on the scanning direction of the signal, the receiving timing and the intensity of the reflected signal from the reflector.

The reflection unit 310 includes an antenna 313, a transmission line 314, an attenuator 315 and a reflector 316. A signal received from the radar 302 by the antenna 313 is reflected by the reflector 316 through the transmission line 314 and the attenuator 315, propagating in the described order. The reflected signal propagates through the attenuator 315 and the transmission line 314, and then is transmitted from the antenna 313 to the radar 302.

The reflection unit 320, as well as the reflection unit 310, includes an antenna 323, a transmission line 324, an attenuator 325 and a reflector 326. A signal received from the radar 302 by the antenna 323 is reflected by the reflector 326 through the transmission line 324 and the attenuator 325, propagating in the described order. The reflected signal propagates through the attenuator 325 and the transmission line 324, and then is transmitted from the antenna 323 to the radar 302.

Figure 32:
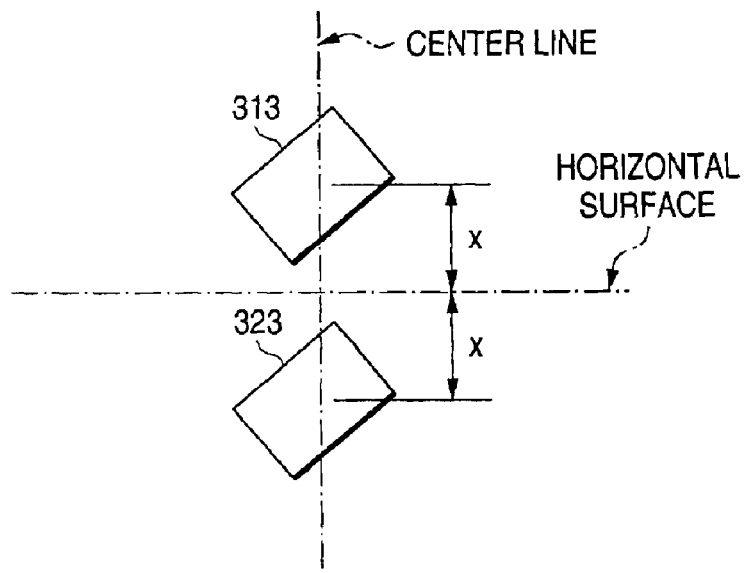
FIG. 32 shows antennas as seen from a radar in the signal transmitting direction.

FIG. 32 shows the antennas 313 and 323 as seen from the radar 302 in the signal transmitting direction. The antennas 313 and 323 are disposed above and below to have a predetermined space x from the horizontal surface of the signal propagating direction from the radar 302. The distances between the radar 302 and the antennas 313 and 323 are the same, and about 1–10 m.

The transmission lines 314 and 324 have different lengths L1 and L2 from each other. The lengths of L1 and L2 are about 1–10 m. In the fifteenth embodiment, for example, L1 is 5 m and L2 is 10 m. The transmission lines 314 and 324 basically have the same characteristics except for the difference of the length. Preferably, the transmission lines 314 and 324 are made of the same material. When the transmission lines 314 and 324 are made of the same material, each of the received signals by the antennas 313 and 314 is attenuated in intensity by a predetermined ratio in accordance with each length L1 or L2. The distance x, and the lengths L1 and L2 of the transmission lines 313 and 314 are not limited in the specific values as described above. These values may be set in accordance with the types of radar, or the range or time discrimination ability of the radar 302.

A transmission line connecting the attenuator 315 with the reflector 316 is the same in the amount of attenuation as a transmission line connecting the attenuator 325 with the reflector 326.

The attenuators 315 and 325 attenuate the signals transmitted through the transmission lines 314 and 324, by predetermined ratios, respectively. When the alignment of the radar 302 is proper, the amounts of attenuation by the transmission lines 314 and 324 are set so that the signals outputted from the antennas 313 and 323 to the radar 302 are the same in intensity.

Unless the attenuators 315 and 325 are provided, the amount of attenuation of the signal in the reflection unit 310 is different from the amount of attenuation of the signal in the reflection unit 320 due to the difference between the length L1 (5 m) of the transmission line 314 and the length L2 (10 m) of the transmission line 324. The attenuators 315 and 325 are provided to attenuate each of the signals to compensate for the difference therebetween. That is, when the signal entering the antenna 313 is the same in intensity as the signal entering the antenna 323, the attenuators 315 and 325 attenuate the signals so that the input-signal/output-signal intensity ratio of the antenna 313 is the same as the input-signal/output-signal intensity ratio of the antenna 323. Namely, the attenuation ratio of the reflection unit 310 is the same as that of the reflection unit 320.

The radio wave absorbers 330 prevent the signal from the radar 302 from being reflected by any members except for the reflection units 310 and 320 and transmitting toward the radar 302. If necessary, additional radio wave absorbers may be provided except for the positions as shown in FIG. 31.

There will be described a mount direction alignment method of the radar 302 using the radar mount direction alignment system 300.

The scanned signal from the radar 302 directed to the antennas 313 and 323 in the horizontal direction are received by the antennas 313 and 323. Since the distance from the radar 302 to the antenna 313 is the same as that of from the radar 302 to the antenna 323, the received intensities of the signals received by antennas 313 and 323 are the same if the alignment of the radar 302 is proper.

The signal received by the antenna 313 is transmitted through the transmission line 314 and the attenuator 315, reflected by the reflector 316, and then outputted from the antenna 313 through the transmission line 314 and the attenuator 315. The signal received by the antenna 323 is transmitted through the transmission line 324 and the attenuator 325, reflected by the reflector 326, and then outputted from the antenna 323 through the transmission line 324 and the attenuator 325. The radar 302 receives the output signals with a timing delay depending on the lengths L1 and L2 of the transmission lines 314 and 315.

When the alignment of the radar 302 is proper, since the signals transmitted through the reflection units 310 and 320 are attenuated by the predetermined ratio, the intensities of the output signals from the reflection units 310 and 320 are the same. Accordingly, the intensities of the received signals from the reflection units 310 and 320 by the radar 302 are the same.

On the other hand, when the alignment of the radar 302 is out of order and the transmitting direction of the signal from the radar 302 is shifted upwardly or downwardly, a difference is generated between the intensities of the signals received by the antenna 313 and antenna 323. Since the reflection units 310 and 320 attenuates the signals by the same ratio, and transmits the attenuated signals toward the radar 302. Accordingly, if the alignment is out of order, the output signals from the antennas 313 and 323 toward the radar 302 are different in intensity, and then the received signals from the reflection units 310 and 320 are also different in intensity.

Figure 33:
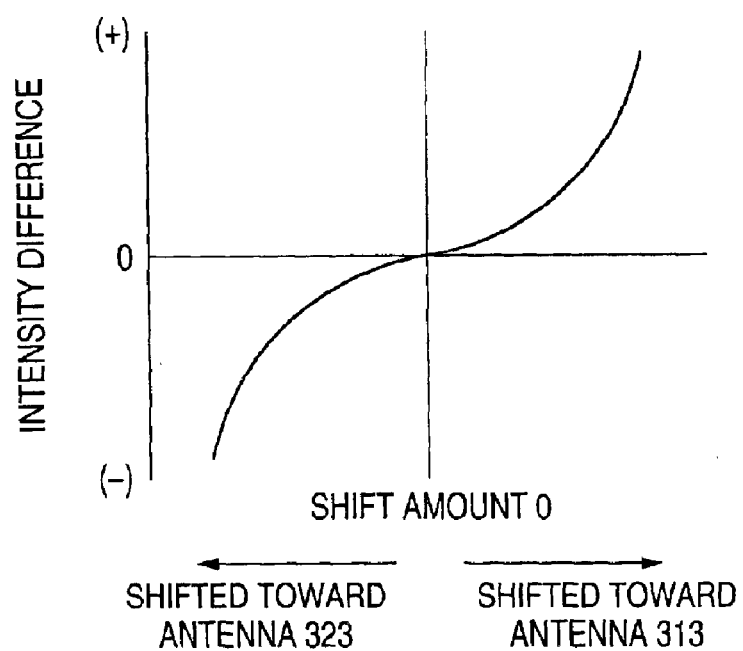
FIG. 33 shows a relation between alignment disorder and intensity difference.

FIG. 33 shows a relation between the alignment disorder and intensity difference between the signals received from the reflection units 310 and 320. The intensity difference is defined by subtracting the intensity of the output signal from the reflection units 320 from the intensity of the output signal from the reflection units 310.

If the intensity difference is in the (+)-region, the signal intensity of the antenna 313 is stronger than that of the antenna 323. This means that the signal transmitting direction of the radar 302 is shifted upwardly. To the contrary, if the intensity difference is in the (−)-region, the signal intensity of the antenna 323 is stronger than that of the antenna 313. This means that the signal transmitting direction of the radar 302 is shifted downwardly.

To adjust the alignment of the radar 302 in actual, the mount direction of the radar 302 is adjusted in order to null the intensity difference. Herewith, the alignment of the radar mount direction is properly adjusted in the vertical direction.

According to the fifteenth embodiment of the present invention, the antennas are positioned above and below with the same distance apart from the radar. Since the transmission lengths in the transmission lines are different in both reflection units, the radar can discriminately receive the each of the output signals from the reflection units. If the ideal distances L1 and L2 of the transmission lines are the same, the radar cannot distinguish the received signals from both reflection units from each other. Namely, if the distances L1 and L2 are the same, the radar cannot determine the received signal having the larger intensity to be transmitted from either of the reflection units even if the radar is disposed in disorder. However, the distances are different, the radar can distinguish the signals from each other since the radar has a function of measuring a distance from the reflection unit and a receiving level that depends on the distance from the reflection unit. To utilize the characteristics, a user can adjust the alignment of the radar mount direction in the vertical direction.

In the fifteenth embodiment, although an attenuator is provided in each of the reflection units 310 and 320, the attenuator may be provided in either of the reflection units, because the length of the transmission line is different and the attenuation ratio of the reflection unit is the same in both of the reflection units.

What is claimed is:

1. A radar mount direction alignment device for aligning a transmit/receive direction of a radar device mounted on a member on which the radar device is mounted, the device comprising:

a receiving section for receiving a signal transmitted from the radar device;

a transmission section for transmitting a signal to the radar device;

a transmission line for transmitting a signal, wherein a predetermined signal is transmitted toward the radar device after a received signal has been transmitted over the transmission line;

a signal transmitting device for transmitting, toward the radar device, a signal which, when the signal transmitted from the radar device is received, behaves as if having been reflected from a reflection target disposed at a position farther from the radar device than a distance between the radar device and the radar mount direction alignment device; and a reflector which reflects a signal entered from one end of the transmission line, at the other end of the transmission line, wherein the reflected signal exits from the one end of the transmission line.

2. The radar mount direction alignment device according to claim 1, wherein the signal transmitting device includes any device for providing a predetermined delay time for the signal received by the receiving section.

3. The radar mount direction alignment device according to claim 1, wherein the transmission line is a member selected from the group consisting of a waveguide, a dielectric line, and an optical fiber.

4. The radar mount direction alignment device according to claim 1, further comprising:

an antenna or lens disposed in an entrance of the transmission line.

5. The radar mount direction alignment device according to claim 1, further comprising:

an amplifier for amplifying a received signal.

6. A radar mount direction alignment device for aligning a transmit/receive direction of a radar device mounted on a member on which the radar device is mounted, the device comprising:

a receiving section for receiving a signal transmitted from the radar device;

a transmission section for transmitting a signal to the radar device;

a signal transmitting device for transmitting, toward the radar device, a signal which, when the signal transmitted from the radar device is received, behaves as if having been reflected from a reflection target disposed at a position farther from the radar device than a distance between the radar device and the radar mount direction alignment device; and a branching device for branching a received signal into a plurality of signals, wherein the respective signals into which the received signal is branched are transmitted toward the radar device.

7. The radar mount direction alignment device according to claim 6, wherein, when the radar mount direction alignment device has the amplifier, the amplifier is disposed upstream of the branching device.

8. A radar mount direction alignment method for aligning a transmit/receive direction of a radar device, the device being mounted on a member on which a radar unit is mounted, the device having a relative angle sensor for sensing a relative angle with reference to a target, the method comprising:

disposing a transmission section at a predetermined position;

detecting an angle relative to the transmission section by the relative angle sensor;

detecting an angle relative to the receiving section detected by the relative angle sensor; and aligning the transmit/receive direction of the radar device in accordance with the angle relative to the transmission section the angle relative to the receiving section.

9. The method of aligning a radar mount direction according to claim 8, wherein a plurality of radar mount direction alignment devices are adopted; and a plurality of transmission sections are disposed at different positions.

10. A radar mount direction alignment method of aligning a transmit/receive direction of a radar device, the device being mounted on a member on which a radar unit is mounted, the device having a signal intensity sensor for receiving a signal reflected from a target and detecting the intensity of the receiving signal, the method comprising:

placing a transmission section at a predetermined position;

detecting the intensity of the signal by the signal intensity sensor; and aligning a transmit/receive direction of the radar device in accordance with the intensity of a signal transmitted from the transmission section.

11. The radar mount direction alignment method according to claim 10, wherein a plurality of radar mount direction alignment devices are adopted; and a plurality of transmission sections are placed at different positions.

12. A radar mount direction alignment method of aligning a transmit/receive direction of a radar device, the device being mounted on a member on which a radar unit is mounted, the device having a signal intensity sensor for detecting the intensity of a signal received from the outside, the method further comprising:

placing a plurality of transmission sections each for transmitting branched signals at different predetermined positions;

detecting the intensity of the signal by the signal intensity sensor; and aligning a transmit/receive direction of the radar device in accordance with the intensity of signals transmitted from the transmission sections.

13. The radar mount direction alignment method according to claim 12, wherein the transmit/receive direction of the radar device is aligned in consideration of a difference in sensitivity in detection of the intensity of signals output from the transmission sections which are susceptible to the influence of distance.

14. The radar mount direction alignment method according to claim 13, wherein, when the radar device is equipped with a relative distance sensor for detecting a distance relative to a target, the sensitivity difference determined on the basis of a relative distance detected by the relative distance sensor is utilized.

15. The radar mount direction alignment method according to claim 13, wherein there is utilized the sensitivity difference that has been determined on the basis of information about a sensitivity difference which has been measured in advance and corresponds to a distance relative to the target.

16. A radar mount direction alignment method for aligning a transmit/receive direction of a radar device, the device being mounted on a member on which a radar unit is mounted, the device having a relative angle sensor for detecting a distance relative to a target, the method comprising:

disposing a reflection target at a predetermined location;

detecting an angle relative to the reflection target by the relative angle sensor; and aligning the transmit/receive direction of the radar device in accordance with the angle relative to the reflection target.

17. The radar mount direction alignment method according to claim 16, wherein the transmit/receive direction of the radar device is aligned such that the angle relative to the target assumes a predetermined angle.

18. The radar mount direction alignment method according to claim 16, wherein the predetermined position is set on substantially a center axis in a sensing area of the radar device.

19. The radar mount direction alignment method according to claim 16, wherein the predetermined position is set on substantially a line connecting the location of a target for alignment with a position at which the radar device is to be mounted.

20. The radar mount direction alignment method according to claim 16, wherein, when the radar device is to be aligned in an azimuth plane, the target is provided in the azimuth plane; or when the radar device is to be aligned in an elevation plane, the reflection target is provided in the elevation plane.

21. The radar mount direction alignment method according to claim 16, wherein a plurality of reflection targets are disposed at different locations.

22. The radar mount direction alignment method according to claim 21, wherein the reflection targets are disposed at positions where signals reflected from the reflection targets exert no influence on each other.

23. The radar mount direction alignment method according to claim 21, wherein the transmit/receive direction of the radar device is aligned in consideration of a difference in sensitivity for detection of the intensity of reflected signals which are susceptible to the influence of distance.

24. The radar mount direction alignment method according to claim 23, wherein, when the radar device is equipped with a relative distance sensor for detecting a distance relative to a target, there is utilized the sensitivity difference determined on the basis of a relative distance detected by the relative distance sensor.

25. A radar device, comprising:

a reflection sensitivity sensor for detecting the intensity of a signal reflected from a target;

a relative distance sensor for detecting a distance relative to the target; and a detection sensitivity difference calculation device for calculating a difference in the sensitivity in detection of the intensity of a reflected signal which is susceptible to the influence of a distance, on the basis of a distance relative to the target detected by the relative distance sensor.

26. The radar device according to claim 25, further comprising:

a memory for storing information about a sensitivity difference which has been determined beforehand and corresponds to a distance relative to the target, wherein the sensitivity difference calculation device determines a difference in sensitivity for detection of intensity of a reflected signal which is susceptible to the influence of distance, on the basis of a distance relative to the target detected by the relative distance sensor and of the information stored in the memory.

27. A radar mount direction alignment method for aligning a transmit/receive direction of a radar device which is mounted on a member on which a radar device is mounted, such as a vehicle, and has a beam scanning function, the method comprising:

disposing a receiving section for receiving a signal transmitted from the radar device at a predetermined position; and detecting a change in the level of a signal received by the receiving section as a result of beam scanning; and aligning the transmit/receive direction of the radar device in accordance with the change in the level of the signal.

28. The radar mount direction alignment method according to claim 27, wherein a signal is transmitted from the radar device toward a center direction of beam scanning.

29. The radar mount direction alignment method according to claim 27, wherein the transmit/receive direction of the radar device is aligned such that the level change assumes a desired level change.

30. The radar mount direction alignment method according to claim 29, wherein the transmit/receive direction of the radar device is aligned such that the level change becomes smaller.

31. The radar mount direction alignment method according to claim 27, wherein the transmit/receive direction of the radar device is aligned with regard to a level change, through use of information about at least one end of scan direction.

32. The radar mount direction alignment method according to claim 27, wherein the transmit/receive direction of the radar device is aligned with regard to a level change without use of information about ends of scan direction.

33. The radar mount direction alignment method according to claim 27, wherein the transmit/receive direction of the radar device is aligned with regard to a level change through use of amplitude information.

34. The radar mount direction alignment method according to claim 27, wherein a plurality of receiving sections are provided at different positions.

35. The radar mount direction alignment method according to claim 27, wherein an unmodulated transmission wave signal is transmitted from the radar device.

36. A radar mount direction alignment device comprising:

a receiving section for receiving a signal; and a converter for converting the frequency of the signal into a lower frequency, the signal including a command for aligning a transmit/receive direction of a radar device.

37. A radar mount direction alignment adjusting device for a radar being mounted on a vehicle and emitting a signal, the radar mount direction alignment adjusting device comprising:

a first reflection unit including:

a first antenna for receiving the signal from the radar and transmitting the signal toward the radar;

a first transmission line for transmitting the signal received by the first antenna;

a first attenuator for attenuating the signal from the first transmission line by a first predetermined ratio; and a first reflector for reflecting the signal from the first attenuator; and a second reflection unit including:

a second antenna for receiving the signal from the radar and transmitting the signal toward the radar;

a second transmission line for transmitting the signal received by the second antenna;

a second attenuator for attenuating the signal from the second transmission line by a second predetermined ratio; and a second reflector for reflecting the signal from the second attenuator, wherein the length of the first transmission line is different from the that of the second transmission line.

38. The radar mount direction alignment adjusting device as claimed in claim 37, wherein the signal reflected by the first reflector is transmitted through the first attenuator and the first transmission line to the first antenna and outputted toward the radar; and the signal reflected by the second reflector is transmitted through the second attenuator and the second transmission line to the second antenna and outputted toward the radar.

39. The radar mount direction alignment adjusting device as claimed in claim 38, wherein the mount direction of the radar is adjusted in accordance with the signals received from the first reflection unit and the second reflection unit.

40. The radar mount direction alignment adjusting device as claimed in claim 37, wherein the first predetermined value of the first attenuator and the second predetermined value of the second attenuator are determined in accordance with the length of the first transmission line and the length of the second transmission line.

41. The radar mount direction alignment adjusting device as claimed in claim 37, wherein the first antenna of the first reflection unit and the second antenna of the second reflection unit are spaced with a same distance from a horizontal surface including the scanning direction of the radar.

42. The radar mount direction alignment adjusting device as claimed in claim 37, wherein the first antenna of the first reflection unit and the second antenna of the second reflection unit are spaced with a same distance from the radar.

43. A method for adjusting alignment of a mount direction of a radar, the method comprising:

receiving a signal from the radar by a first reflection unit;

transmitting a first signal from the first reflection unit to the radar, the signal corresponding to a first distance;

receiving the signal from the radar by a second reflection unit;

transmitting a second signal from the second reflection unit to the radar, the second signal corresponding to a second distance; and adjusting the alignment of the radar in accordance with the first signal and the second signal.

* * * * *